(12) United States Patent
Matsuda

(10) Patent No.: US 10,608,753 B2
(45) Date of Patent: Mar. 31, 2020

(54) ULTRASONIC DIAGNOSTIC APPARATUS, PROBE HEAD, ULTRASONIC PROBE, ELECTRONIC MACHINE, AND ULTRASONIC DIAGNOSTIC APPARATUS

(71) Applicant: SEIKO EPSON CORPORATION, Tokyo (JP)

(72) Inventor: Hiroshi Matsuda, Gifu (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 15/818,068

(22) Filed: Nov. 20, 2017

(65) Prior Publication Data
US 2018/0091235 A1    Mar. 29, 2018

Related U.S. Application Data

(63) Continuation of application No. 14/055,003, filed on Oct. 16, 2013, now abandoned.

(30) Foreign Application Priority Data

Oct. 17, 2012 (JP) ................................. 2012-229586

(51) Int. Cl.
*H04R 15/00* (2006.01)
*H04B 11/00* (2006.01)
(Continued)

(52) U.S. Cl.
CPC ............ *H04B 11/00* (2013.01); *A61B 8/4483* (2013.01); *B06B 1/0207* (2013.01);
(Continued)

(58) Field of Classification Search
None
See application file for complete search history.

(56) References Cited

U.S. PATENT DOCUMENTS 3,803,336 A * 4/1974 Williams ................. G09B 9/56
434/9
5,460,181 A * 10/1995 Seyed-Bolorforosh ......................
B06B 1/0622
128/916

(Continued)

FOREIGN PATENT DOCUMENTS

EP          1629778 A1    3/2006
JP      2005-152608 A    6/2005
(Continued)

OTHER PUBLICATIONS

Seo, Chi Hyung, and Jesse T. Yen. "A 256×256 2-D array transducer with row-column addressing for 3-D rectilinear imaging." IEEE transactions on ultrasonics, ferroelectrics, and frequency control 56.4 (2009). (Year: 2009).*

(Continued)

*Primary Examiner* — Hovhannes Baghdasaryan
*Assistant Examiner* — Jonathan D Armstrong
(74) *Attorney, Agent, or Firm* — Global IP Counselors, LLP

(57) ABSTRACT

An ultrasonic measurement apparatus has an ultrasonic transducer device including an ultrasonic element array, a first through n-th first end-side terminal XA1 to XAn provided to a first end side, and a first through n-th second end-side terminal XB1 to XBn provided to a second end side opposing the first end side; a first transmission circuit outputting first drive signals VTA1 to VTAn to the first through n-th first end-side terminals XA1 to XAn; and a second transmission circuit outputting second drive signals VTB1 to VTBn to the first through n-th second end-side terminals XB1 to XBn.

17 Claims, 15 Drawing Sheets

(51) Int. Cl.
*A61B 8/00* (2006.01)
*G01N 29/06* (2006.01)
*G01N 29/26* (2006.01)
*B06B 1/02* (2006.01)
*B06B 1/06* (2006.01)
*G01S 7/52* (2006.01)
*G01S 15/89* (2006.01)

(52) U.S. Cl.
CPC ....... *B06B 1/0622* (2013.01); *G01N 29/0654* (2013.01); *G01N 29/262* (2013.01); *G01S 7/5202* (2013.01); *G01S 15/8925* (2013.01); *A61B 8/4405* (2013.01); *A61B 8/4411* (2013.01); *A61B 8/4427* (2013.01); *B06B 2201/20* (2013.01); *B06B 2201/55* (2013.01); *B06B 2201/76* (2013.01); *G01S 7/5208* (2013.01); *G01S 7/52082* (2013.01)

(56) References Cited

U.S. PATENT DOCUMENTS

| | | | |
|---|---|---|---|
| 5,524,626 A | 6/1996 | Liu | |
| 5,797,845 A | 8/1998 | Barabash et al. | |
| 5,851,187 A * | 12/1998 | Thomas, III | G01S 15/8959 600/447 |
| 6,160,340 A * | 12/2000 | Guo | B06B 1/0629 310/334 |
| 6,310,832 B1 * | 10/2001 | Kits van Heyningen | G01S 3/8083 367/122 |
| 6,343,129 B1 | 1/2002 | Pelrine et al. | |
| 6,775,388 B1 * | 8/2004 | Pompei | B06B 1/0292 367/181 |
| 7,561,321 B2 | 7/2009 | Heald | |
| 8,100,015 B2 | 1/2012 | Karasawa et al. | |
| 2003/0048698 A1 | 3/2003 | Barnes et al. | |
| 2004/0160144 A1 | 8/2004 | Daft et al. | |
| 2005/0131302 A1 * | 6/2005 | Poland | A61B 8/14 600/459 |
| 2007/0016026 A1 | 1/2007 | Thomenius et al. | |
| 2007/0291964 A1 | 12/2007 | Chien et al. | |
| 2008/0021324 A1 * | 1/2008 | Seto | A61B 8/00 600/447 |
| 2008/0029688 A1 | 2/2008 | Yagi et al. | |
| 2008/0049954 A1 | 2/2008 | Hansen et al. | |
| 2008/0067895 A1 * | 3/2008 | Adachi | A61B 8/12 310/324 |
| 2008/0089180 A1 | 4/2008 | Matsumoto et al. | |
| 2009/0043206 A1 * | 2/2009 | Towfiq | A61B 8/0825 600/447 |
| 2009/0058228 A1 | 3/2009 | Wakabayashi et al. | |
| 2009/0126494 A1 | 5/2009 | Karasawa et al. | |
| 2009/0182233 A1 | 7/2009 | Wodnicki | |
| 2011/0021920 A1 * | 1/2011 | Shafir | A61B 8/54 600/447 |
| 2011/0252890 A1 | 10/2011 | Matsuda | |
| 2012/0188849 A1 | 7/2012 | Matsuda et al. | |
| 2013/0324853 A1 | 12/2013 | Matsuda | |
| 2015/0094590 A1 | 4/2015 | Kiyose et al. | |
| 2015/0094596 A1 | 4/2015 | Kiyose et al. | |
| 2017/0003384 A1 * | 1/2017 | Christiansen | B06B 1/0215 |
| 2017/0285156 A1 * | 10/2017 | Yigang | A61B 8/00 |

FOREIGN PATENT DOCUMENTS

| | | |
|---|---|---|
| JP | 2006-061252 A | 3/2006 |
| JP | 2012-152319 A | 8/2012 |
| WO | 2009/073561 A1 | 6/2009 |
| WO | 2013/136212 A1 | 9/2013 |

OTHER PUBLICATIONS

Daher, Nadim Michel, and Jesse T. Yen. "2-D array for 3-D ultrasound imaging using synthetic aperture techniques." IEEE transactions on ultrasonics, ferroelectrics, and frequency control 53.5 (2006): 912-924. (Year: 2006).*

Daher et al.; "2-D Array for 3-D Ultrasound Imaging Using Synthetic Aperture Techniques"; IEEE Transactions on Ultrasonics, Ferroelectrics, and Frequency Control, vol. 53, No. 5, May 2006; pp. 912-924.

Seo et al.; "64×64 2-D array transducer with row-column addressing" 2006 IEEE Ultrasonics Symposium; pp. 74-77.

Seo et al.; "256×256 2-D array tansducer with row-column addressing for 3-D imaging" 2007 IEEE Ultrasonics Symposium; pp. 2381-2384.

Seo et al.; "A 256×256 2-D Array Transducer with Row-Column Addressing for 3-D Rectilinear Imaging" 2009 IEEE Transactions on Ultrasonics, Ferroelectrics, and Frequency Control, vol. 56, Nov. 4, Apr. 2009; pp. 837-847.

* cited by examiner

ULTRASONIC DIAGNOSTIC APPARATUS, PROBE HEAD, ULTRASONIC PROBE, ELECTRONIC MACHINE, AND ULTRASONIC DIAGNOSTIC APPARATUS

CROSS-REFERENCE TO RELATED APPLICATIONS

This application is a continuation application of U.S. patent application Ser. No. 14/055,003, filed on Oct. 16, 2013. This application claims priority to Japanese Patent Application No. 2012-229586 filed on Oct. 17, 2012. The entire disclosure of Japanese Patent Application No. 2012-229586 is hereby incorporated herein by reference.

BACKGROUND

Technical Field

The present invention relates to an ultrasonic measurement apparatus, ultrasonic probe, electronic machine, ultrasonic diagnostic apparatus, and the like.

Related Art

One known example of an apparatus for insonifying a subject with ultrasonic waves and receiving reflected waves coming from an interfacial surface at which the acoustic impedance is different within the interior of the subject is an ultrasonic diagnostic apparatus for inspecting the interior of a human body. As an ultrasonic apparatus (ultrasonic probe) to be used in an ultrasonic diagnostic apparatus, Japanese Laid-open Patent Publication 2006-61252 discloses a technique for scanning a beam in a row direction and in a column direction by arraying piezoelectric elements in a matrix array shape and providing a wiring for every row and column.

However, in the technique disclosed in Japanese Laid-open Patent Publication 2006-61252, it is necessary, inter alia, to control the delay in the row direction to match the signal delay in the column direction, thus increasing the scale of circuitry for the signal generation circuit, among other problems.

SUMMARY

According to several modes of the present invention, it is possible to provide an ultrasonic measurement apparatus, a probe head, an ultrasonic probe, an electronic machine, an ultrasonic diagnostic apparatus, and the like enabling efficient scanning with a simple configuration.

According an aspect of the present invention, an ultrasonic measurement apparatus includes: an ultrasonic transducer device including an ultrasonic element array, a first first end-side terminal through an n-th (where n is an integer two or greater) first end-side terminal provided to a first end side of the ultrasonic element array, and a first second end-side terminal through an n-th second end-side terminal provided to a second end side of the ultrasonic element array opposing the first end side of the ultrasonic element array; a first transmission circuit configured to output first drive signals to the first first end-side terminal through the n-th first end-side terminal; and a second transmission circuit configured to output second drive signals to the first second end-side terminal through the n-th second end-side terminal. An amplitude of at least one of the first drive signals and the second drive signals is variably set.

According to the aspect of the invention, the amplitude of at least one of the first drive signals and the second drive signals is variably set by the first and second transmission circuits, and thus a peak position of an intensity distribution of the ultrasonic waves emitted from the ultrasonic transducer device can be changed. As a result, it becomes possible to implement an ultrasonic measurement apparatus enabling efficient scanning with a simple configuration.

According to another aspect of the invention, a set position of a scan plane, which is a plane running along a direction of scanning of a beam of ultrasonic waves emitted from the ultrasonic transducer device, may be changed by changing of a difference between an amplitude of the first drive signals and an amplitude of the second drive signals by at least one of the first transmission circuit and the second transmission circuit.

In so doing, the set position of the scan plane can be changed by the first and second transmission circuit, and thus a plurality of scan planes can be set along, for example, a slice direction, making it possible inter alia to obtain a plurality of cross-sectional images by scanning the ultrasonic beam along each of the scan planes. As a result, it becomes possible to implement an ultrasonic measurement apparatus enabling efficient scanning with a simple configuration.

According to another aspect of the invention, the at least one of the first transmission circuit and the second transmission circuit may set the scan plane to a first set position by causing the amplitude of the first drive signals to be greater than the amplitude of the second drive signals, and set the scan plan to a second set position different from the first set position by causing the amplitude of the first drive signals to be less than the amplitude of the second drive signals.

In so doing, the scan plane can be set to the first set position or the second set position by the first and second transmission circuits, and thus the scan plane can be set to a desired position to scan the ultrasonic beam.

According to another aspect of the invention, the at least one of the first transmission circuit and the second transmission circuit may set the scan plane to a third set position between the first set position and the second set position, by causing the amplitude of the first drive signals and the amplitude of the second drive signals to be the same.

In so doing, the scan plane can be set to be between the first set position and the second set position by the first and second transmission circuits, and thus the scan plan can be set to a desired position to scan the ultrasonic beam.

According to another aspect of the invention, the first transmission circuit may output the first drive signals, which are for carrying out a phase scanning, and the second transmission circuit may output the second drive signals, which are for carrying out the phase scanning.

In so doing, the scan plane can be a set to a desired position to scan the ultrasonic beam by phase scanning along the set scan plane.

According to another aspect of the invention, the first transmission circuit may output the first drive signals, which are for carrying out a linear scanning, and the second transmission circuit may output the second drive signals, which are for carrying out the linear scanning.

In so doing, the scan plane can be a set to a desired position to scan the ultrasonic beam by linear scanning along the set scan plane.

According to another aspect of the invention, the ultrasonic measurement apparatus may further include a first flexible substrate connected to the first first end-side terminal through the n-th first end-side terminal and a second flexible substrate connected to the first second end-side terminal through the n-th second end-side terminal. The first transmission circuit is implemented on the first flexible substrate, and the second transmission circuit is implemented on the second flexible substrate.

In so doing, the space for mounting the first and second transmission circuits can be reduced. The first and second flexible substrates can also be bent for the mounting. As a result, it becomes possible to reduce the size of the ultrasonic measurement apparatus.

According to another aspect of the invention, the ultrasonic element array may include a first ultrasonic element group through an n-th ultrasonic element group arranged along a first direction A first end-side node of a j-th (where j is an integer 1≤j≤n) ultrasonic element group of the first ultrasonic element group through the n-th ultrasonic element group is connected to a j-th first end-side terminal of the first first end-side terminal through the n-th first end-side terminal. A second end-side node of the j-th ultrasonic element group is connected to a j-th second end-side terminal of the first second end-side terminal through the n-th second end-side terminal. The j-th ultrasonic element group includes a plurality of ultrasonic elements and a drive electrode line which is wired along a second direction intersecting the first direction, a first end of which is connected to the first end-side node, and a second end of which is connected to the second end-side node. A first electrode belonging to each of the plurality of the ultrasonic elements of the j-th ultrasonic element group is connected to the drive electrode line.

In so doing, the plurality of ultrasonic elements of the j-th ultrasonic element group can be driven by the first drive signals inputted to the j-th first end-side terminal and the second drive signals inputted to the j-th second end-side terminal.

According to another aspect of the invention may include a common voltage generation circuit configured to output common voltages. The ultrasonic transducer device includes a first common voltage terminal through an m-th (where m is an integer two or greater) common voltage terminal. The ultrasonic element array includes a first common electrode line through an m-th common electrode line wired along the first direction and connected to the first common voltage terminal through the m-th common voltage terminal. The second electrode belonging to each of the plurality of the ultrasonic elements of the j-th ultrasonic element group is connected to one of the first common electrode line through the m-th common electrode line. The common voltage generation circuit outputs the common voltages, of mutually different voltages, to the first common voltage terminal through the m-th common voltage terminal.

In so doing, the supplying of the common voltages of mutually different voltages by the common voltage generation circuit makes it possible to change the set position of the scan plane. As a result, the set position of the scan plane can be variably set within a broader range.

According to another aspect of the invention, the ultrasonic transducer device may include a substrate on which a plurality of openings are arranged in an arrayed shape. Each of the plurality of the ultrasonic elements belonging to the j-th ultrasonic element group is provided to each of the plurality of the openings. Each of the plurality of the ultrasonic elements includes a vibrating membrane for blocking of one of the openings and a piezoelectric element section provided on the vibrating membrane. The piezoelectric element section includes a lower electrode provided on the vibrating membrane, a piezoelectric body membrane at least partially covering the lower electrode, and an upper electrode at least partially covering the piezoelectric body membrane. The first electrode is either the upper electrode or the lower electrode.

In so doing, supplying of the first drive signals and the second drive signals to the upper electrode or the lower electrode causes the piezoelectric body membrane to expand and contract due to the first and second drive signals and causes the vibrating membrane to vibrate, thus allowing the ultrasonic elements to emit ultrasonic waves.

According to another mode of the invention, a probe head includes any of the ultrasonic measurement apparatuses described above.

According to another mode of the invention, an ultrasonic probe includes the probe head described above and a processing apparatus for processing the signals coming from the ultrasonic measurement apparatus.

According to another mode of the invention, an electronic machine includes any of the ultrasonic probes described above.

According to another mode of the invention, an ultrasonic diagnostic apparatus includes the ultrasonic probe described above and a display unit for displaying display image data.

BRIEF DESCRIPTION OF THE DRAWINGS

Referring now to the attached drawings which form a part of this original disclosure.

DETAILED DESCRIPTION OF EXEMPLARY EMBODIMENTS

The following describes in greater detail a preferred embodiment of the present invention. The present embodiment described below is not, however, meant to gratuitously limit the content of the present invention described in the claims, nor is the entire configuration described in the present embodiment necessarily essential in terms of the solution of the present invention.

1. Ultrasonic Transducer Element

Figure 1A:
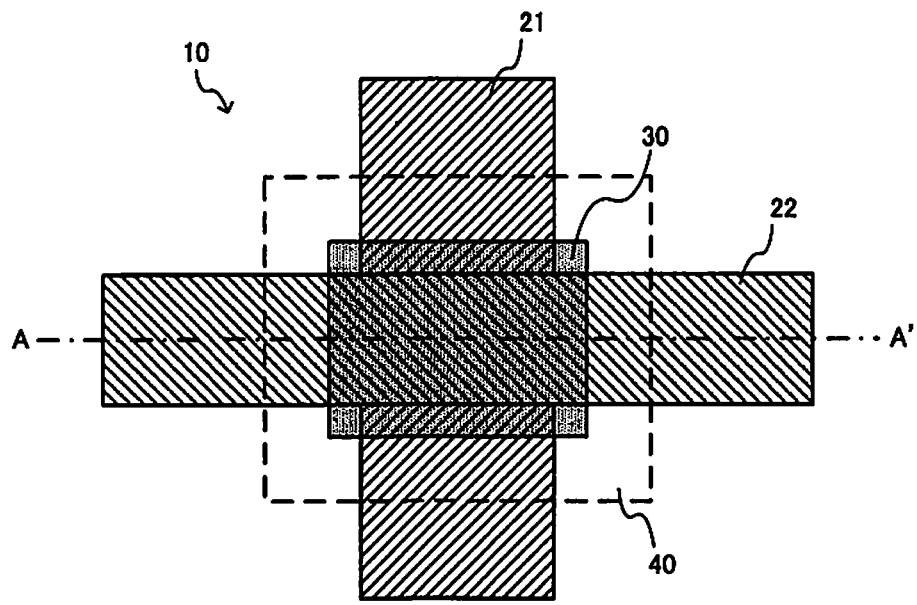
FIG. 1A is an example of a basic configuration for an ultrasonic transducer element.
Figure 1B:
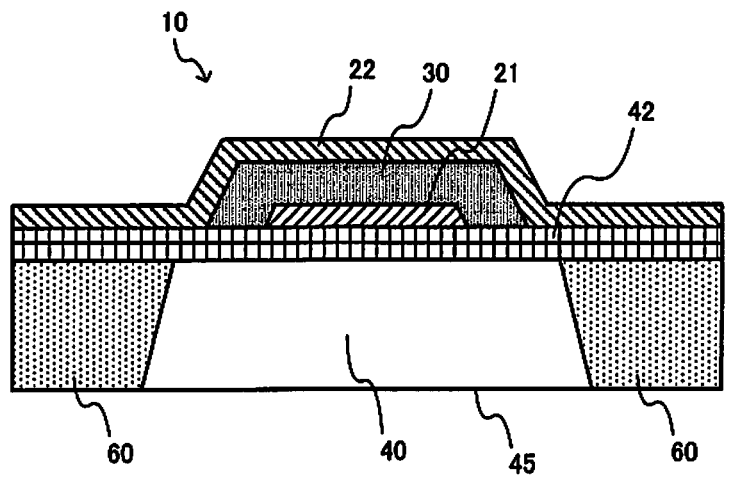
FIG. 1B and FIG. 1C show the example of the basic configuration for the ultrasonic transducer element.

FIGS. 1A and 1B illustrate examples of a basic configuration for an ultrasonic transducer element (a thin-film piezoelectric ultrasonic transducer element) 10 belonging to the present embodiment. The ultrasonic transducer element 10 of the present embodiment includes a vibrating membrane (membrane, support membrane) 42 and a piezoelectric element section. The piezoelectric element section includes a lower electrode (first electrode layer) 21, a piezoelectric body membrane (piezoelectric body layer) 30, and an upper electrode (second electrode layer) 22. The ultrasonic element 10 of the present embodiment is not limited to being the configuration of FIGS. 1A and 1B, but rather a variety of modifications can be implemented, such as omitting a part of the constituent elements thereof, replacing same with other constituent elements, or adding other constituent elements.

In the following description, the ultrasonic transducer element 10 is also called an "ultrasonic element 10".

Figure 1C:
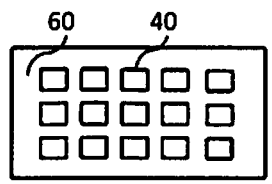

FIG. 1A is a plan view of the ultrasonic element 10, which is formed on a substrate (silicon substrate) 60, as seen from a direction perpendicular to a substrate on an element formation surface side. FIG. 1B is a cross-sectional view illustrating a cross-section taken along the A-A' line in FIG. 1A. FIG. 1C is a plan view of the substrate 60 in which a plurality of openings are formed.

The first electrode layer 21 is formed of, for example, a metal thin film, on an upper layer of the vibrating membrane 42. The first electrode layer 21 may be a wiring that extends to the outside of an element formation region, as illustrated in FIG. 1A, and is connected to an adjacent ultrasonic element 10.

The piezoelectric body membrane 30 is formed of, for example, a lead zirconate titanate (PZT) thin film, and is provided so as to at least partially cover the first electrode layer 21. The material of the piezoelectric body membrane 30, however, is not limited to being PZT, but rather, for example, lead titanate (PbTiO3), lead zirconate (PbZrO3), lanthanum lead titanate ((Pb, La)TiO3), or the like may be used.

The second electrode layer 22 is formed of, for example, a metal thin film, and is provided so as to at least partially cover the piezoelectric body membrane 30. The second electrode layer 22 may be a wiring that extends to the outside of the element formation region, as illustrated in FIG. 1A, and is connected to an adjacent ultrasonic element 10.

The vibrating membrane (membrane) 42 is provided so that an opening 45 is closed off by, for example, a two-layered structure of an SiO2 thin film and a ZrO2 thin film. The vibrating membrane 42 supports the piezoelectric body membrane 30 and the first and second electrode layers 21, 22, and is able to vibrate in conformity with the expansion and contraction of the piezoelectric body membrane 30 to generate ultrasonic waves.

The opening 45 is arranged on the substrate 60. A cavity region 40 created by the opening 45 is formed by etching by reactive ion etching (RIE) or the like from a reverse side of the substrate 60 (the side on which the element is not formed).

The lower electrode of the ultrasonic element 10 is formed of the first electrode layer 21 and the upper electrode is formed of the second electrode layer 22. More specifically, the portion of the first electrode layer 21 that is covered by the piezoelectric body membrane 30 forms the lower electrode, and the portion of the second electrode layer 22 that covers the piezoelectric body membrane 30 forms the upper electrode. That is to say, the piezoelectric body membrane 30 is provided sandwiched between the lower electrode and the upper electrode.

The piezoelectric body membrane 30 is expanded and contracted in an in-plane direction by the application of a voltage between the lower electrode and the upper electrode, i.e., between the first electrode layer 21 and the second electrode layer 22. The ultrasonic element 10 uses a monomorph (unimorph) structure obtained by bonding together a thin piezoelectric element section and the vibrating membrane 42, and when the piezoelectric element section undergoes in-plane expansion and contraction, warping takes place because the dimensions of the vibrating membrane 42 remain unaffected. As such, applying an alternating current voltage to the piezoelectric body membrane 30 causes the vibrating membrane 42 to vibrate with respect to the film thickness direction, and the vibration of the vibrating membrane 42 causes ultrasonic waves to be emitted. The voltage that is applied to the piezoelectric body membrane 30 is, for example, 10 to 30 V, and the frequency is, for example, 1 to 10 MHz.

In contrast to the fact that the drive voltage for bulk ultrasonic elements would be about 100 V in peak-to-peak, the drive voltage could be reduced to about 10 to 30 V in peak-to-peak in a thin-film piezoelectric ultrasonic element 10 as is illustrated in FIGS. 1A and 1B.

The ultrasonic element 10 also operates as a receiver element for receiving an ultrasonic echo produced when emitted ultrasonic waves are reflected by a subject and then come back. The ultrasonic echo causes the vibrating membrane 42 to vibrate, and this vibration causes a pressure to be applied to the piezoelectric body membrane 30 and causes a voltage to be generated between the lower electrode and the upper electrode. This voltage can be extracted as a receipt signal.

2. Ultrasonic Measurement Apparatus

Figure 2:
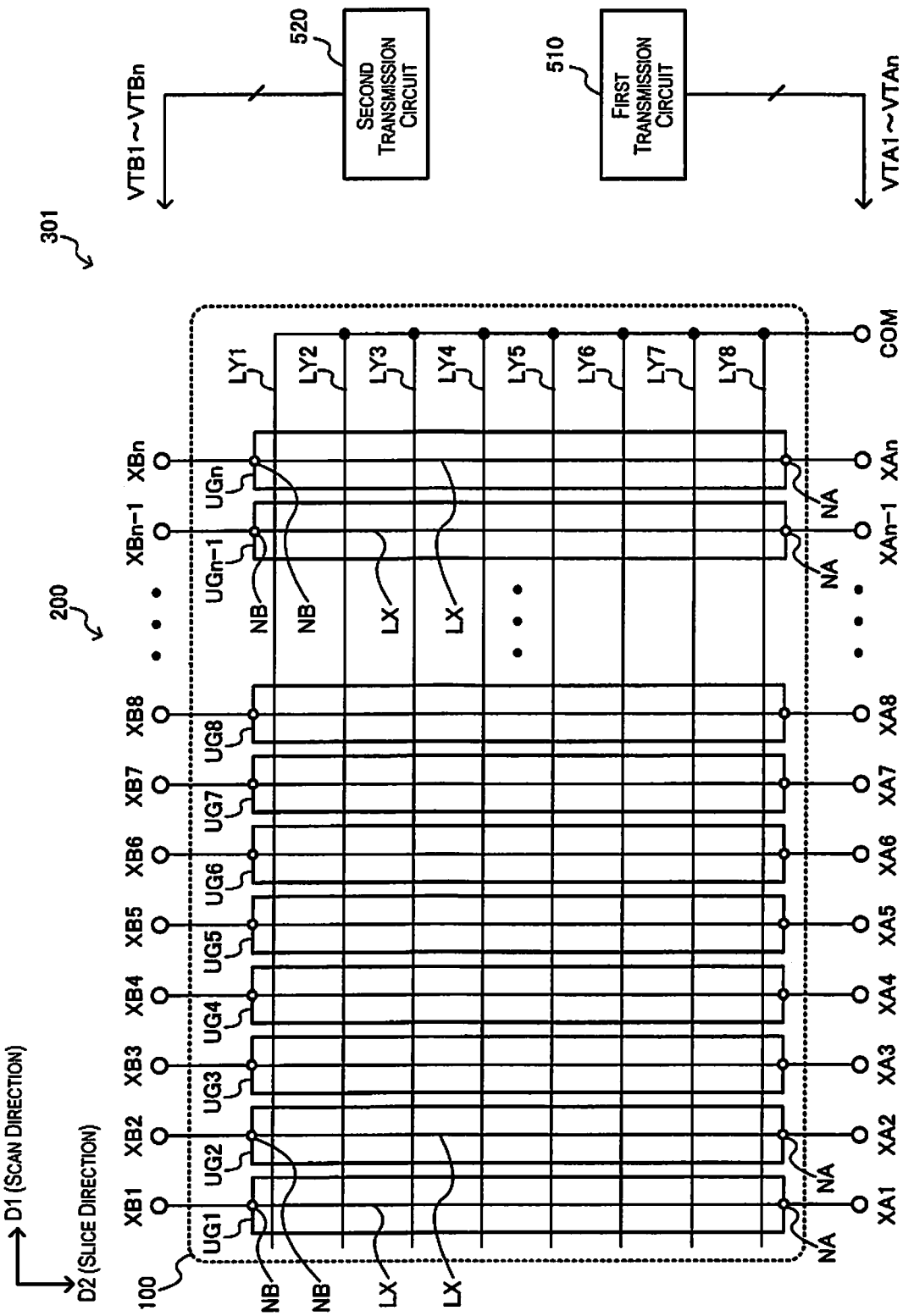
FIG. 2 is a first example of a configuration of an ultrasonic measurement apparatus.

FIG. 2 illustrates a first configuration example for an ultrasonic measurement apparatus 301 of the present embodiment. The ultrasonic measurement apparatus 301 comprises an ultrasonic transducer device 200, a first transmission circuit 510, and a second transmission circuit 520. The ultrasonic transducer device 200 comprises: the substrate 60, on which a plurality of the opening 45 are arranged in an array shape; a ultrasonic element array 100; a first through n-th (where n is an integer two or greater) end-side terminal XA1 to XAn; a first through n-th second end-side terminal XB1 to XBn; and a common electrode terminal COM. The ultrasonic measurement apparatus 301 of the present embodiment is not limited to being the configuration of FIG. 2, but rather a variety of modifications can be implemented, such as omitting a part of the constituent elements thereof, replacing same with other constituent elements, or adding other constituent elements.

The ultrasonic element array 100 includes a first through n-th ultrasonic element group (ultrasonic transducer element group) UG1 to UGn arranged along a first direction, and first through m-th (where m is an integer two or greater) common electrode lines LY1 to LYm which are wired along the first direction D1 and are connected in common to the common voltage terminal COM. FIG. 2 illustrates a case where m=8, by way of example.

Each of the ultrasonic element groups of the first through n-th ultrasonic element groups UG1 to UGn includes a plurality of ultrasonic elements 10 and a drive electrode line LX which is wired along a second direction D2 that intersects the first direction D1. One end of the drive electrode line LX is connected to a first end-side node NA, and the other end is connected to a second end-side node NB. An example of the configuration of the ultrasonic element groups UG1 to UGn shall be described below.

The first end-side node NA of a j-th (where j is an integer $1 \leq j \leq n$) ultrasonic element group UGj of the first through n-th ultrasonic element groups UG1 to UGn is connected to the j-th first end-side terminal XAj of the first through n-th first end-side terminals XA1 to XAn. The second end-side node NB of the j-th ultrasonic element group UGj is connected to the j-th second end-side terminal XBj of the first through n-th second end-side terminal XB1 to XBn.

The first transmission circuit 510 outputs first drive signals VTA1 to VTAn to the first through n-th first end-side terminals XA1 to XAn. The second transmission circuit 520 outputs second drive signals VTB1 to VTBn to the first through n-th second end-side terminals XB1 to XBn. A common voltage VCOM is also supplied to the common voltage terminal COM. The common voltage VCOM should be a constant direct current voltage, and need not be 0 V, i.e., a ground potential.

The first transmission circuit 510 is able to output first drive signals VTA1 to VTAn which are for carrying out phase scanning (sector scanning), and the second transmission circuit 520 is able to output second drive signal VTB1 to VTBn which are for carrying out phase scanning. The first transmission circuit 510 is also able to output first drive signals VTA1 to VTAn which are for carrying out linear scanning, and the second transmission circuit 520 is also able to output second drive signals VTB1 to VTBn which are for carrying out linear scanning. A more detailed description of the phase scanning and the linear scanning shall be provided below.

The ultrasonic measurement apparatus 301 of the present embodiment is able to variably set the amplitude of the first drive signals VTA1 to VTAn and/or of the second drive signals VTB1 to VTBn. More specifically, the first transmission circuit 510 carries out a first amplitude control for controlling the amplitude of the first drive signals VTA1 to VTAn, and the second transmission circuit 520 carries out a second amplitude control for controlling the amplitude of the second drive signals VTB1 to VTBn. The amplitude of the first drive signals VTA1 to VTAn and/or of the second drive signals VTB1 to VTBn can also be variably set by the first and/or second amplitude control.

Changing the difference between the amplitude of the first drive signals VTA1 to VTAn and the amplitude of the second drive signals VTB1 to VTBn using the transmission circuit amplitude control of the first transmission circuit 510 and/or the second transmission circuit 520 allows the ultrasonic measurement apparatus 301 of the present embodiment to change the set position of a scan plane, which is a plane that runs along a scan direction (for example, in FIG. 2, the first direction D1) of the beam of ultrasonic waves emitted from the ultrasonic transducer device 200. The set position of the scan plane refers to, for example, a Y-coordinate position of the scan plane in a case where the first direction D1 of FIG. 2 (the scan direction) is an X-coordinate direction and the second direction D2 is a Y-coordinate direction. That is to say, the set position of the scan plane can be represented by a Y-coordinate of the scan plane. The relationship between the set position of the scan plane and the amplitude of the first drive signals VTA1 to VTAn and amplitude of the second drive signals VTB1 to VTBn shall be described in greater detail below.

Figure 3B:
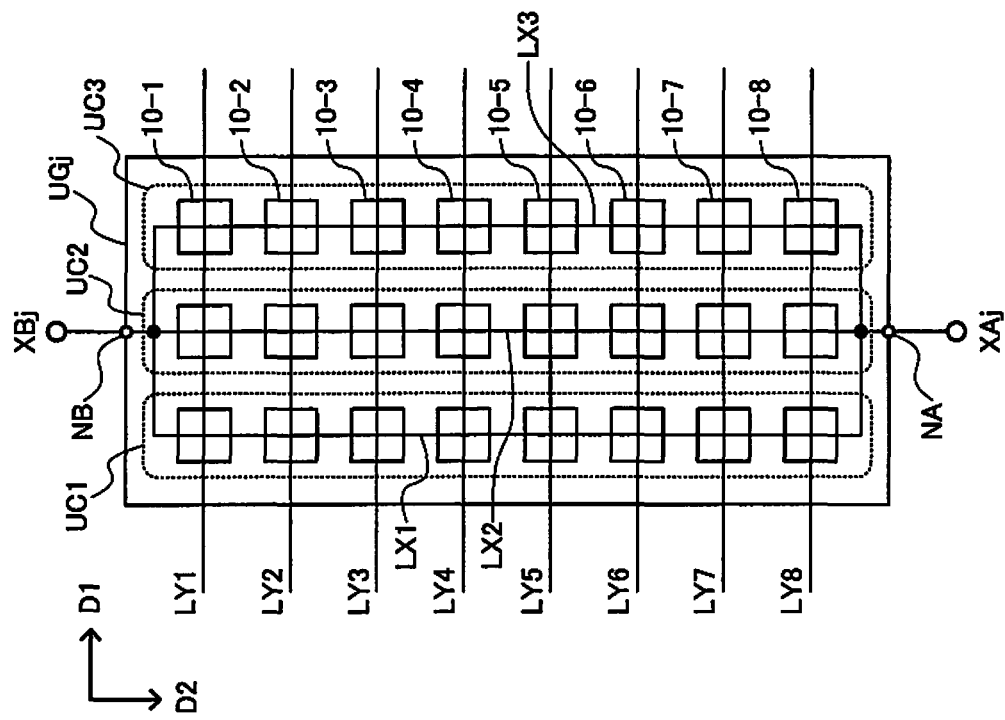
FIG. 3B is the example of the j-th ultrasonic element group.
Figure 3A:
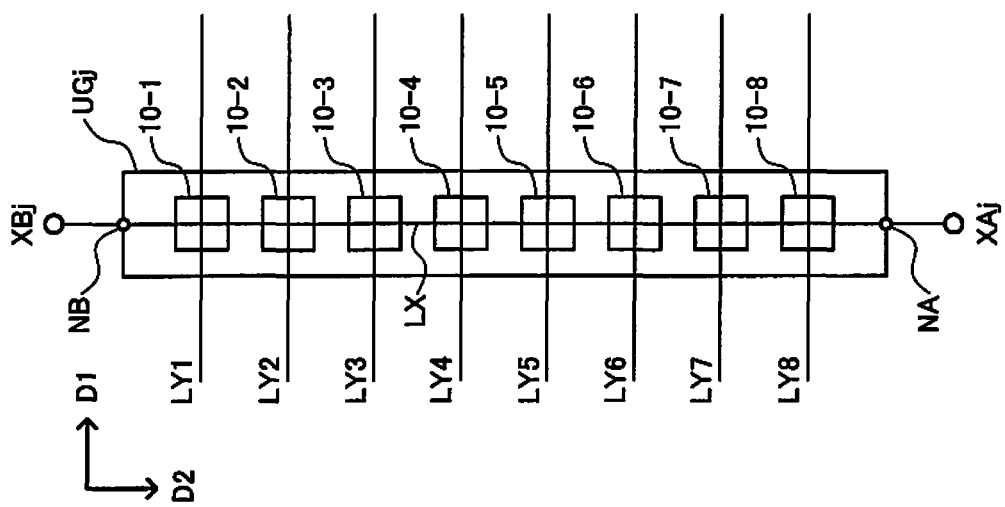
FIG. 3A is an example of a j-th ultrasonic element group.

FIGS. 3A and 3B illustrate examples of the configuration of the j-th ultrasonic element group UGj. The ultrasonic element group UGj illustrated in FIG. 3A comprises eight (more broadly, m) ultrasonic elements 10-1 to 10-8 arranged along the second direction D2 and the drive electrode line LX wired along the second direction D2. The eight ultrasonic elements 10-1 to 10-8 and the drive electrode line LX can also be collectively called an "ultrasonic element column UC". That is to say, the ultrasonic element group UGj illustrated in FIG. 3A comprises one ultrasonic element column UC.

The first electrode of each of the ultrasonic elements 10 is connected to the drive electrode line LX, and the second electrode is connected to the corresponding common electrode line of the first through eighth (more broadly, first through m-th) common electrode lines LY1 to LY8. For example, the first electrode of a first ultrasonic element 10-1 of the eight ultrasonic elements 10-1 to 10-8 is connected to the drive electrode line LX, and the second electrode is connected to the first common electrode line LY1. The first electrode of the fourth ultrasonic element 10-4 is connected to the drive electrode line LX, and the second electrode is connected to the fourth common electrode line LY4.

One end of the drive electrode line LX is connected to the first end-side node NA, and the other end is connected to the second end-side node NB. The first end-side node NA is connected to the j-th first end-side terminal XAj, and the second end-side node NB is connected to the j-th second end-side terminal XBj.

The ultrasonic element group UGj illustrated in FIG. 3B comprises three ultrasonic element columns UC1 to UC3 arranged along the first direction D1. Each of the ultrasonic element columns UC1 to UC3 comprises the eight (more broadly, m) ultrasonic elements 10-1 to 10-8 arranged along the second direction D2. The ultrasonic element columns UC1 to UC3 further comprise drive electrode lines LX1 to LX3 wired along the second direction D2.

The first electrode of each of the ultrasonic elements 10 is connected to the corresponding drive electrode line of the drive electrode lines LX1 to LX3, and the second electrode is connected to the corresponding common electrode line of the first through m-th common electrode lines LY1 to LYm. For example, the first electrode of the first ultrasonic element 10-1 of the first ultrasonic element column UC1 is connected to the first drive electrode line LX1, and the second electrode is connected to the first common electrode line LY1. The first electrode of the fourth ultrasonic element 10-4 of the third ultrasonic element column UC3 is connected to the third drive electrode line LX3, and the second electrode is connected to the fourth common electrode line LY4.

One end of each of the drive electrode lines LX1 to LX3 is connected to the first end-side node NA, and the other end is connected to the second end-side node NB. The first end-side node NA is connected to the j-th first end-side terminal XAj, and the second end-side node NB is connected to the j-th second end-side terminal XBj.

The ultrasonic element columns UC which the ultrasonic element group UGj comprises is not limited to being of the numbers illustrated in FIGS. 3A and 3B, but rather may be two in number or may be four or more in number. In a case where the ultrasonic element group UGj comprises a plurality of ultrasonic element columns UC, then the number of ultrasonic elements possessed by each of the ultrasonic element columns UC need not be the same.

In this manner, the ultrasonic element groups UG of the present embodiment include the plurality of ultrasonic elements 10, as well as the one or plurality of drive electrode lines LX wired along the second direction, with the one end connected to the first end-side node NA and the other end connected to the second end-side node NB. The first electrode possessed by each of the plurality of ultrasonic elements 10 of the ultrasonic element groups UG is connected to the one, or to one of the plurality of, drive electrode line(s) LX, and the second electrode is connected to one of the first through m-th common electrode lines LY1 to LYm. The first electrode of the ultrasonic elements 10 is, for example, either one of the upper electrode or the lower electrode illustrated in FIGS. 1A and 1B, and the second electrode of the ultrasonic elements 10 is the other of the upper electrode and the lower electrode different from the first electrode.

The first end-side node NA of the j-th ultrasonic element group UGj is connected to the j-th first end-side terminal XAj. The second end-side node NB of the j-th ultrasonic element group UGj is connected to the j-th second end-side terminal XBj. In so doing, each of the ultrasonic elements 10 of the j-th ultrasonic element group UGj is driven by the first drive signal VTAj supplied to the j-th first end-side terminal XAj and by the second drive signal VTBj supplied to the j-th second end-side terminal XBj.

In the ultrasonic measurement apparatus 301 of the present embodiment, the direction of emission of the ultrasonic waves can be changed by the phase scanning (sector scanning).

Figure 4:
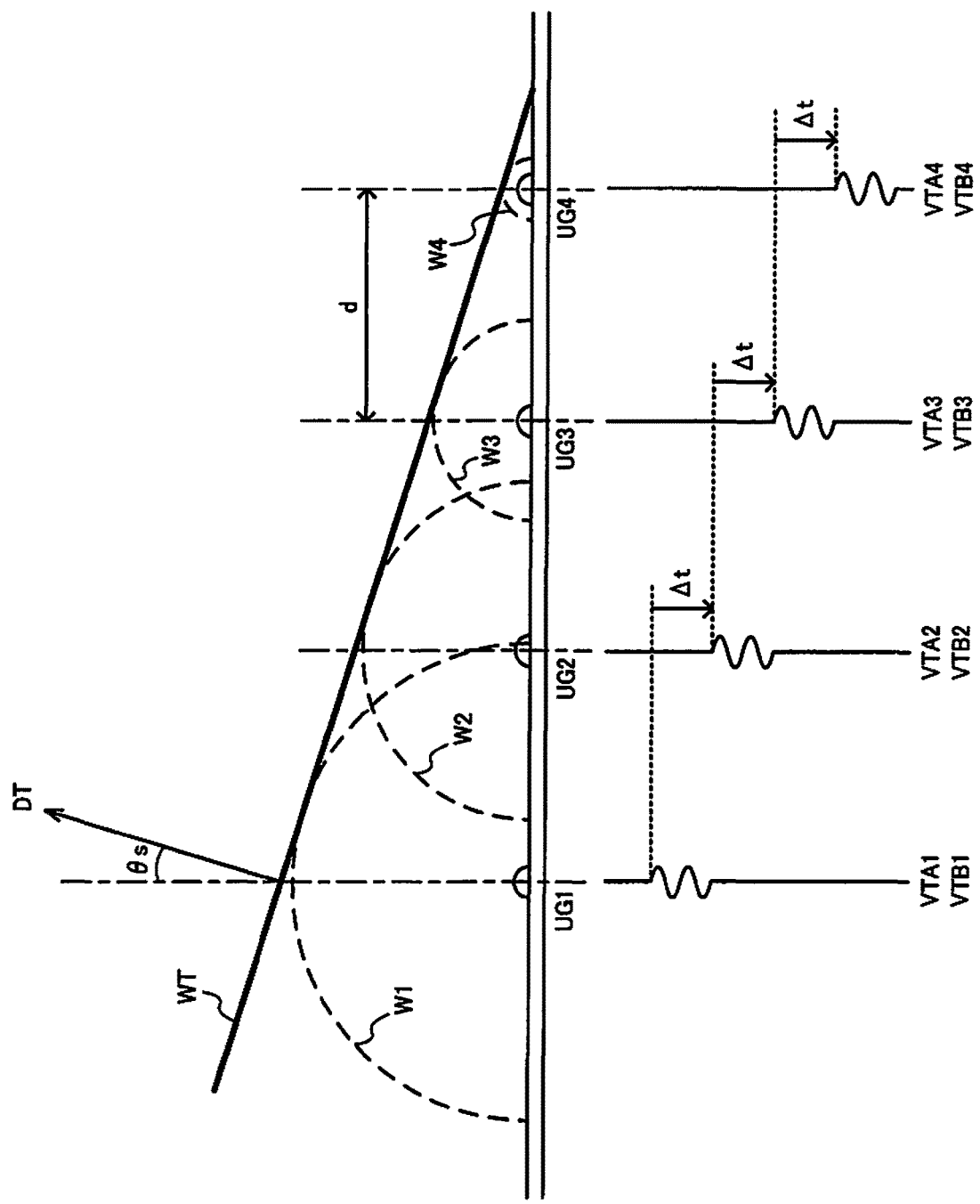
FIG. 4 is a drawing for describing a phase scanning.

FIG. 4 is a drawing for describing the phase scanning in the ultrasonic measurement apparatus 301 of the present embodiment. For the sake of simplicity, four ultrasonic element groups UG1 to UG4 are described in FIG. 4. The ultrasonic element groups UG1 to UG4 are arranged at equal intervals d. The phase of the first drive signals VTA1 to VTA4 being supplied is earliest for VTA1, with a delay increasing commensurate with a predetermined difference of phase occurring in VTA2, then VTA3, and then VTA4, in the stated order. That is to say, the first drive signals VTA to VTA4 are supplied in association with a predetermined time difference Δt in the order of VTA1, then VTA2, then VTA3, and then VTA4. Similarly, the second drive signals VTB1 to VTB4 are supplied in association with the predetermined time difference Δt in the order of VTB1, then VTB2, then VTB3, and then VTB4. The first and second drive signal (for example, VTA1 and VTB1) for driving the same ultrasonic element group (for example, UG1 are of the same phase and are supplied at the same timing.

FIG. 4 illustrates wave fronts W1 to W4, at a certain point in time, for ultrasonic waves emitted from each of the ultrasonic element groups UG1 to UG4. The ultrasonic waves emitted from each of the ultrasonic element groups are composited to form a wave front WT of a composited ultrasonic wave. A direction of radiation DT of the wave front WT will be the direction of emission of the composited ultrasonic waves (the beam direction). An angle θs formed by the beam direction DT and the normal direction of the array plane is given by:

$$\sin\theta s = c \times \Delta t / d \quad (1)$$

Herein, c, Δt, and d are the speed of sound, the time difference of the drive signals, and the element spacing, respectively.

Thus, phase scanning, i.e., changing the phase difference (time difference) in the drive signals being supplied to each of the ultrasonic element groups makes it possible to change the beam direction. More specifically, for example, in the configuration example illustrated in FIG. 2, changing the phase difference (time difference) between each of the signals for the first drive signals VTA1 to VTAn and the second drive signals VTB1 to VTBn makes it possible to scan the beam direction along the first direction D1. That is to say, the first direction D1 is the scan direction for the phase scanning, and the second direction D2 is a slice direction.

Figure 5:
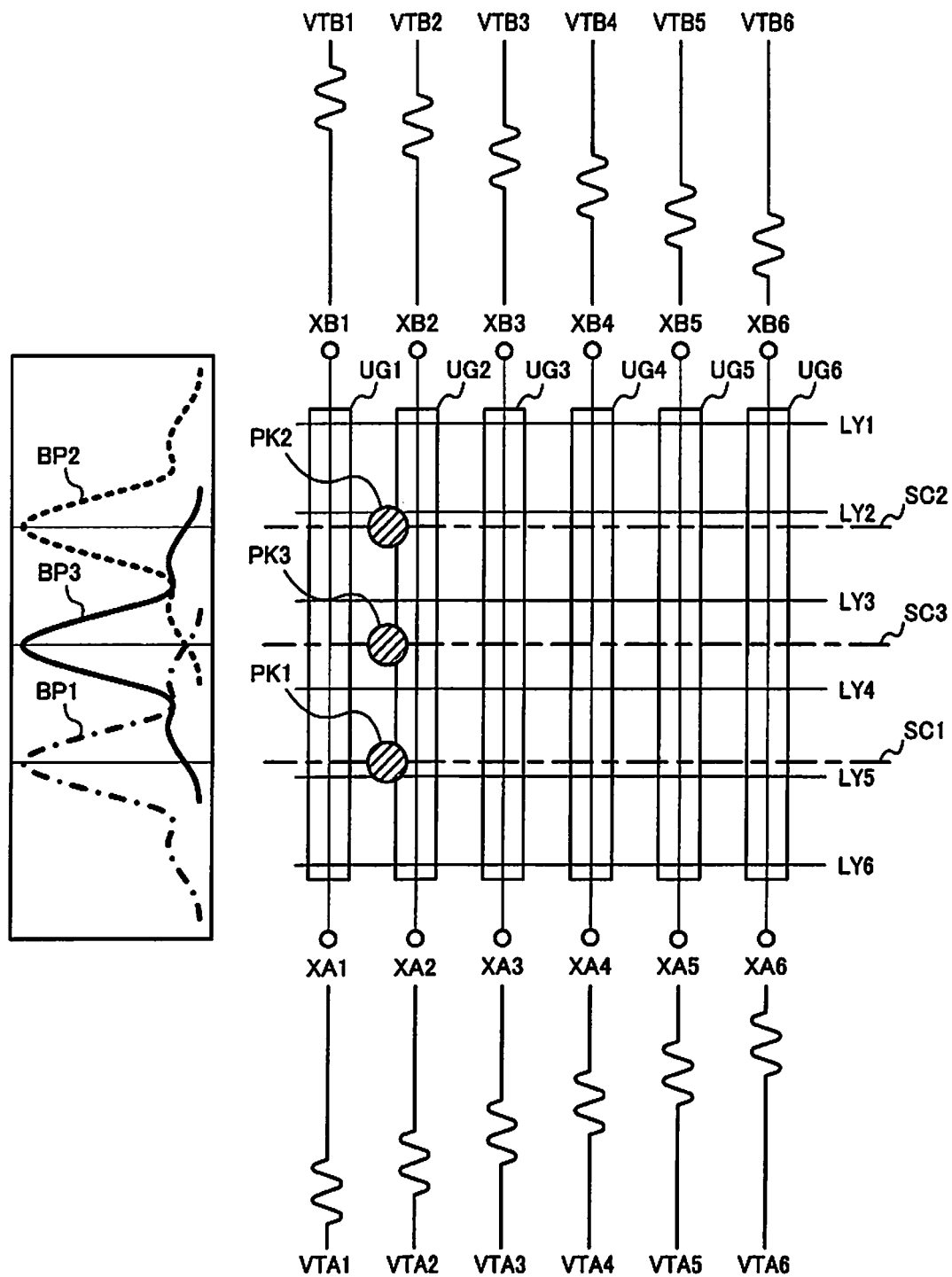
FIG. 5 is a first drawing for describing an intensity distribution of ultrasonic waves in a case of phase scanning.

FIG. 5 is a first drawing for describing the intensity distribution (beam profile) of the ultrasonic waves in a case of phase scanning in the ultrasonic measurement apparatus 301 of the present embodiment. FIG. 5, for the sake of simplicity, describes the ultrasonic element array 100 constituted of the first through sixth ultrasonic element groups UG1 to UG6 and the first through sixth common electrode lines LY1 to LY6.

The first drive signals VTA1 to VTA6 are supplied so that the VTA6 is earliest, becoming increasingly delayed by the predetermined time difference from VTA6 toward VTA1. Similarly, the second drive signals VTB1 to VTB6 are supplied so that the VTB6 is earliest, becoming increasingly delayed by the predetermined time difference from VTB6 toward VTB1. The first and second drive signal (for example, VTA1 and VTB1) for driving the same ultrasonic element group (for example, UG1) are supplied at the same timing. So doing causes the phase scanning described above to shift the intensity distribution of the ultrasonic waves in the inverse direction of the first direction D1. For example, as illustrated in FIG. 5, the peak position of the intensity distribution of the ultrasonic waves is positioned at PK1, PK2, or PK3. The peak positions PK1, PK2, and PK3 will be described below.

As stated above, according to the ultrasonic measurement apparatus 301 of the present embodiment, it is possible to variably set the amplitude of the first drive signals VTA1 to VTAn and/or the second drive signals VTB1 to VTBn. That is to say, the difference between the amplitude of the first drive signals VTA1 to VTAn and the amplitude of the second drive signals VTB1 to VTBn can be variably set. In the following description, the amplitude of the first drive signals VTA1 to VTAn is understood to be VA, and the amplitude of the second drive signals VTB1 to VTBn is understood to be VB.

In a case where VA>VB, then the amplitude of the drive voltage applied to the ultrasonic element 10 closest to the first end-side terminals XA1 to XA6 is greatest, and, conversely, the amplitude of the drive voltage applied to the ultrasonic element 10 closest to the second end-side terminals XB1 to XB6 is smallest. For example, in the case of FIG. 3A, the amplitude of the drive voltage applied to the ultrasonic element 10-8 is greatest, and the amplitudes of the drive voltages applied toward the ultrasonic element 10-1 become gradually smaller. As such, the ultrasonic wave intensity emitted from the ultrasonic element 10-8 is highest, and the ultrasonic wave intensities emitted going toward the ultrasonic element 10-1 become gradually lower. As such, the peak position of the intensity distribution of the ultrasonic waves is shifted in the second direction D2. For example, as illustrated in FIG. 5, the peak position of the intensity distribution of the ultrasonic waves is positioned at PK1. The beam profile running along the second direction D2 in this case will be, for example, what is illustrated by BP1.

In a case where VA<VB, then the amplitude of the drive voltage applied to the ultrasonic element 10 closest to the second end-side terminals XB1 to XB6 is greatest, and, conversely, the amplitude of the drive voltage applied to the ultrasonic element 10 closest to the first end-side terminals XA1 to XA6 is smallest. As such, the peak position of the intensity distribution of the ultrasonic waves is shifted in the inverse direction of the second direction D2, conversely to the preceding description. For example, as illustrated in FIG. 5, the peak position of the intensity distribution of the ultrasonic waves is positioned at PK2. The beam profile running along the second direction D2 in this case will be, for example, what is illustrated by BP2.

In a case where VA=VB, then the amplitude of the drive voltage applied to each of the ultrasonic elements 10 is identical, and thus, for example, as illustrated in FIG. 5, the peak position of the intensity distribution of the ultrasonic waves is positioned between PK1 and PK2, e.g., at PK3. The beam profile running along the second direction D2 in this case will be, for example, what is illustrated by BP3.

Figure 6:
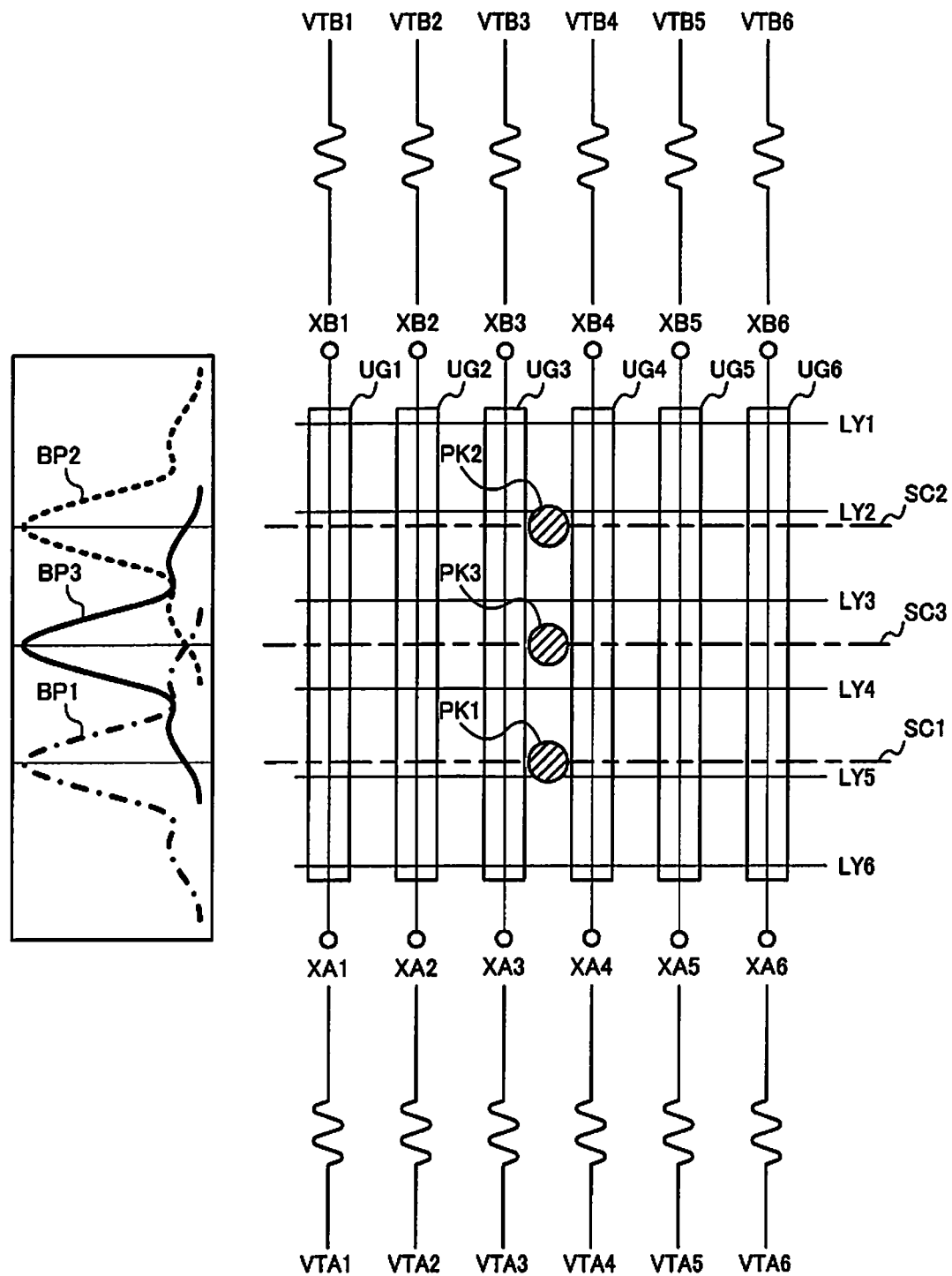
FIG. 6 is a second drawing for describing an intensity distribution of ultrasonic waves in a case of phase scanning.

FIG. 6 is a second drawing for describing the intensity distribution (beam profile) of the ultrasonic waves in the case of ultrasonic scanning. The first drive signals VTA1 to VTA6 and the second drive signals VTB1 to VTB6 are supplied at the same timing, i.e., without a phase difference (time difference). As such, the ultrasonic waves emitted from each of the ultrasonic element groups are consistent in terms of phase, and thus the peak position of the intensity distribution of the ultrasonic waves will be PK1, PK2, or PK3, for example, as illustrated in FIG. 6.

When VA is the amplitude of the first drive signals VTA1 to VTAn and VB is the amplitude of the second drive signals VTB1 to VTBn, similarly with respect to the case of FIG. 5, then in a case where VA>VB, the peak position of the intensity distribution of the ultrasonic waves will be, for example, PK1. The beam profile running along the second direction D2 in this case will be, for example, what is illustrated by BP1. In a case where VA<VB, then the peak position of the intensity distribution of the ultrasonic waves will be, for example, PK2. The beam profile running along the second direction D2 in this case will be, for example, what is illustrated by BP2. In a case where VA=VB, then the peak position of the intensity distribution of the ultrasonic waves will be, for example, PK3. The beam profile running along the second direction D2 in this case will be, for example, what is illustrated by BP3.

Figure 7:
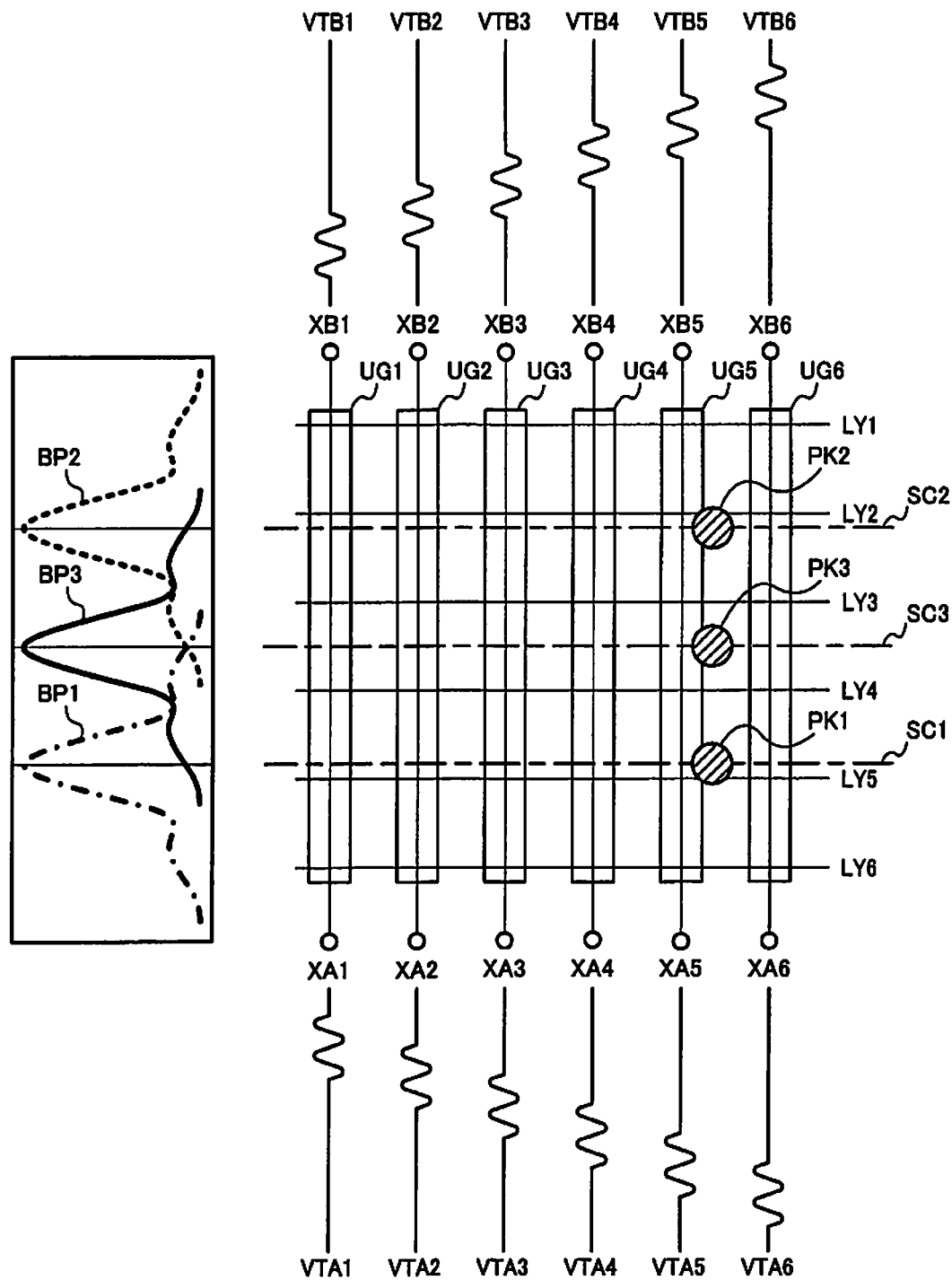
FIG. 7 is a third drawing for describing an intensity distribution of ultrasonic waves in a case of phase scanning.

FIG. 7 is a third drawing for describing the intensity distribution (beam profile) of the ultrasonic waves in a case of ultrasonic scanning. The first drive signals VTA1 to VTA6 are supplied so that the VTA1 is earliest, becoming increasingly delayed by the predetermined time difference from VTA1 toward VTA6. Similarly, the second drive signals VTB1 to VTB6 are supplied so that the VTB1 is earliest, becoming increasingly delayed by the predetermined time difference from VTB1 toward VTB6. The first and second drive signal (for example, VTA1 and VTB1) for driving the same ultrasonic element group (for example, UG1) are supplied at the same timing. So doing causes the phase scanning described above to shift the intensity distribution of the ultrasonic waves in the first direction D1. For example, as illustrated in FIG. 7, the peak position of the intensity distribution of the ultrasonic waves is positioned at PK1, PK2, or PK3.

When VA is the amplitude of the first drive signals VTA1 to VTAn and VB is the amplitude of the second drive signals VTB1 to VTBn, similarly with respect to the case of FIGS. 5 and 6, then in a case where VA>VB, the peak position of the intensity distribution of the ultrasonic waves will be, for example, PK1. The beam profile running along the second direction D2 in this case will be, for example, what is illustrated by BP1. In a case where VA<VB, then the peak position of the intensity distribution of the ultrasonic waves will be, for example, PK2. The beam profile running along the second direction D2 in this case will be, for example, what is illustrated by BP2. In a case where VA=VB, then the peak position of the intensity distribution of the ultrasonic waves will be, for example, PK3. The beam profile running along the second direction D2 in this case will be, for example, what is illustrated by BP3.

As will be readily understood from FIGS. 5, 6, and 7, in the case of the phase scanning, then changing the difference between the amplitude VA of the first drive signals VTA1 to VTAn and the amplitude VB of the second drive signals VTB1 to VTBn allows the first transmission circuit 510 and/or the second transmission circuit 520 to change the set position of the scan plane, which is the plane running along the scan direction (for example, the first direction D1) of the beam of ultrasonic waves emitted from the ultrasonic transducer device 200.

More specifically, causing the amplitude of the first drive signals VTA1 to VTAn to be greater than the amplitude of the second drive signals VTB1 to VTBn allows the first transmission circuit 510 and/or the second transmission circuit 520 to set the scan plane to, for example, a first set position SC1 illustrated in FIGS. 5, 6, and 7. Causing the amplitude of the first drive signals VTA1 to VTAn to be less than the amplitude of the second drive signals VTB1 to VTBn allows the first transmission circuit 510 and/or the second transmission circuit 520 to set the scan plane to, for example, a second set position SC2 illustrated in FIGS. 5, 6, and 7. Causing the amplitude of the first drive signals VTA1 to VTAn and the amplitude of the second drive signals VTB1 to VTBn to be the same allows the first transmission circuit 510 and/or the second transmission circuit 520 to set the scan plane to, for example, a third set position SC3 between the first set position SC1 and the second set position SC2 illustrated in FIGS. 5, 6, and 7.

In the ultrasonic measurement apparatus 301 of the present embodiment, the direction of emission of the ultrasonic waves can be changed by the linear scanning.

Figure 8:
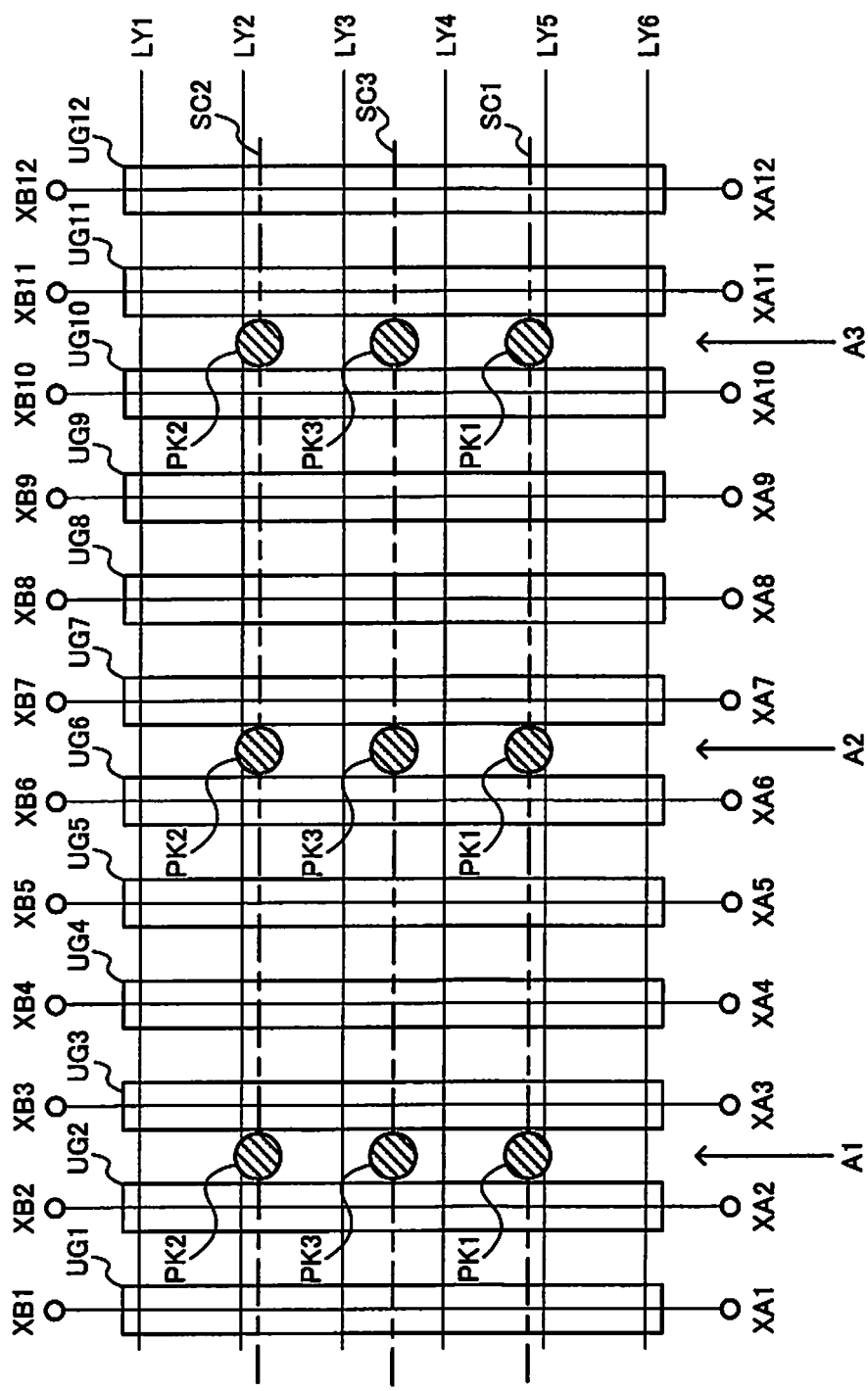
FIG. 8 is a drawing for describing an intensity distribution of ultrasonic waves in a case of linear scanning.

FIG. 8 is a drawing for describing the intensity distribution (beam profile) of the ultrasonic waves in the case of the linear scanning in the ultrasonic measurement apparatus 301 of the present embodiment. FIG. 8, for the sake of simplicity, describes the ultrasonic element array 100 constituted of the first through twelfth ultrasonic element groups UG1 to UG12 and the first through sixth common electrode lines LY1 to LY6.

In the case of the linear scanning, the ultrasonic element groups that are within a predetermined region (a region intended to be driven) are driven, and the ultrasonic element groups that are outside of the predetermined region are not driven. Moving the region intended to be driven along, for example, the first direction D1 makes it possible to scan the peak position of the ultrasonic waves along the first direction D1 (the scan direction).

In FIG. 8, when, for example, the ultrasonic element groups UG1 to UG4 are intended to be driven, the first transmission circuit 510 supplied the first drive signals VTA1 to VTA4 to the first end-side terminals XA1 to XA4, and the second transmission circuit 520 supplies the second drive signals VTB1 to VTB4 to the second end-side terminals XB1 to XB4. The peak position of the intensity distribution of the ultrasonic waves at this time will be, for example, the PK1, PK2, or PK3 illustrated in A1 of FIG. 8.

In a case where VA>VB, where VA is the amplitude of the first drive signals VTA1 to VTA4 and VB is the amplitude of the second drive signals VTB1 to VTB4, then the peak position of the intensity distribution of the ultrasonic waves will be, for example, the PK1 illustrated in A1 of FIG. 8. The beam profile running along the second direction D2 in this case will be, for example, what is illustrated by BP1. In a case where VA<VB, then the peak position of the intensity distribution of the ultrasonic waves will be, for example, the PK2 illustrated in A1 of FIG. 8. The beam profile running along the second direction D2 in this case will be, for example, what is illustrated by BP2. In a case where VA=VB, then the peak position of the intensity distribution of the ultrasonic waves will be, for example, the PK3 illustrated in A1 of FIG. 8. The beam profile running along the second direction D2 in this case will be, for example, what is illustrated by BP3.

When, for example, the ultrasonic element groups UG5 to UG8 are intended to be driven, then the first transmission circuit 510 supplies the first drive signals VTA5 to VTA8 to the first end-side terminals XA5 to XA8, and the second transmission circuit 520 supplies the second drive signals VTB5 to VTB8 to the second end-side terminals XB5 to XB8. The peak position of the intensity distribution of the ultrasonic waves at this time will be, for example, the PK1, PK2, or PK3 illustrated in A2 of FIG. 8.

In a case where VA>VB, where VA is the amplitude of the first drive signals VTA5 to VTA8 and VB is the amplitude of the second drive signals VTB5 to VTB8, then the peak position of the intensity distribution of the ultrasonic waves will be, for example, the PK1 illustrated in A2 of FIG. 8. The beam profile running along the second direction D2 in this case will be, for example, what is illustrated by BP1. In a case where VA<VB, then the peak position of the intensity distribution of the ultrasonic waves will be, for example, the PK2 illustrated in A2 of FIG. 8. The beam profile running along the second direction D2 in this case will be, for example, what is illustrated by BP2. In a case where VA=VB, then the peak position of the intensity distribution of the ultrasonic waves will be, for example, the PK3 illustrated in A2 of FIG. 8. The beam profile running along the second direction D2 in this case will be, for example, what is illustrated by BP3.

When, for example, the ultrasonic element groups UG9 to UG12 are intended to be driven, then the first transmission circuit 510 supplies the first drive signals VTA9 to VTA12 to the first end-side terminals XA9 to XA12, and the second transmission circuit 520 supplies the second drive signals VTB9 to VTB12 to the second end-side terminals XB9 to XB12. The peak position of the intensity distribution of the ultrasonic waves at this time will be, for example, the PK1, PK2, or PK3 illustrated in A3 of FIG. 8.

In a case where VA>VB, where VA is the amplitude of the first drive signals VTA9 to VTA12 and VB is the amplitude of the second drive signals VTB9 to VTB12, then the peak position of the intensity distribution of the ultrasonic waves will be, for example, the PK1 illustrated in A3 of FIG. 8. The beam profile running along the second direction D2 in this case will be, for example, what is illustrated by BP1. In a case where VA<VB, then the peak position of the intensity distribution of the ultrasonic waves will be, for example, the PK2 illustrated in A3 of FIG. 8. The beam profile running along the second direction D2 in this case will be, for example, what is illustrated by BP2. In a case where VA=VB, then the peak position of the intensity distribution of the ultrasonic waves will be, for example, the PK3 illustrated in A3 of FIG. 8. The beam profile running along the second direction D2 in this case will be, for example, what is illustrated by BP3.

Thus, in the case of the linear scanning, too, changing the difference between the amplitude VA of the first drive signals VTA1 to VTAn and the amplitude VB of the second drive signals VTB1 to VTBn allows the first transmission circuit 510 and/or the second transmission circuit 520 to change the set position of the scan plane, which is the plane running along the scan direction (for example, the first direction D1) of the beam of ultrasonic waves emitted from the ultrasonic transducer device 200.

More specifically, causing the amplitude of the first drive signals VTA1 to VTAn to be greater than the amplitude of the second drive signals VTB1 to VTBn allows the first transmission circuit 510 and/or the second transmission circuit 520 to set the scan plane to, for example, a first set position SC1 illustrated in FIG. 8. Causing the amplitude of the first drive signals VTA1 to VTAn to be less than the amplitude of the second drive signals VTB1 to VTBn allows the first transmission circuit 510 and/or the second transmission circuit 520 to set the scan plane to, for example, a second set position SC2 illustrated in FIG. 8. Causing the amplitude of the first drive signals VTA1 to VTAn and the amplitude of the second drive signals VTB1 to VTBn to be the same allows the first transmission circuit 510 and/or the second transmission circuit 520 to set the scan plane to, for example, a third set position SC3 between the first set position SC1 and the second set position SC2 illustrated in FIG. 8.

Figure 9:
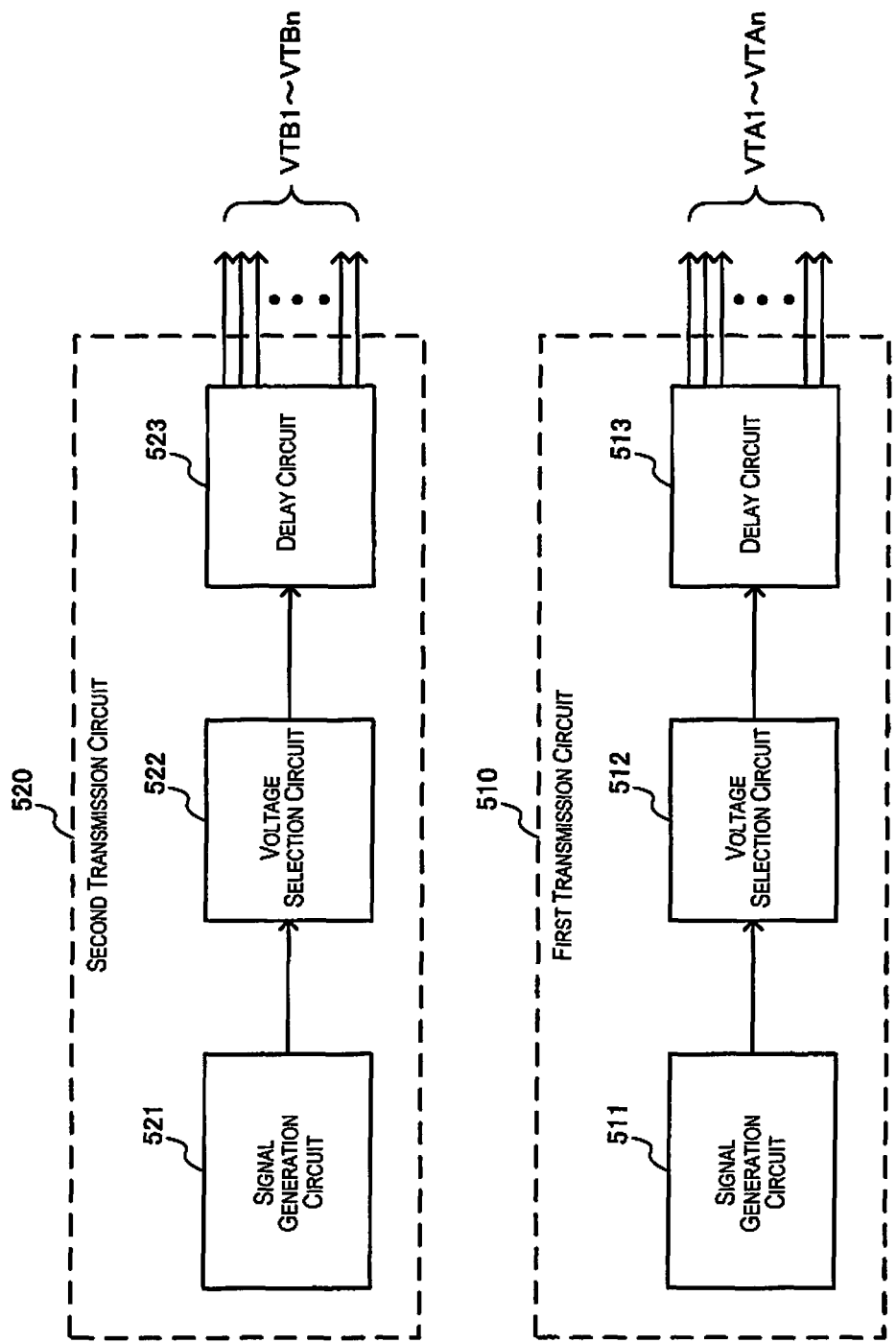
FIG. 9 is a first example of a configuration of a first and second transmission circuit.

FIG. 9 illustrates an example of a first configuration for the first and second transmission circuits 510, 520 of the present embodiment. The first transmission circuit 510 comprises a signal generation circuit 511, a voltage selection circuit 512, and a delay circuit 513. The second transmission circuit 520 comprises a signal generation circuit 521, a voltage selection circuit 522, and a delay circuit 523. The first and second transmission circuits 510 and 520 of the present embodiment are not limited to being the configuration of FIG. 9, but rather a variety of modifications can be implemented, such as omitting a part of the constituent elements thereof, replacing same with other constituent elements, or adding other constituent elements.

The signal generation circuit 511 is, for example, a pulser (a pulse generator), and outputs a sine wave pulse, square wave pulse, triangle wave pulse, or the like.

The voltage selection circuit 512 receives a pulse signal coming from the signal generation circuit 511, selects a voltage for regulating the amplitude of the pulse signal, and outputs a pulse signal having an amplitude based on the selected voltage. The voltage selection circuit 512 can be constituted of, for example, a resistive divider circuit comprising a resistive element and a switch element. The voltage for regulating the amplitude of the pulse signal is selected by, for example, a control signal coming from a transmission and receipt control unit 334 (FIG. 14) described below.

The delay circuit 513 receives the pulse signal coming from the voltage selection circuit 512 and outputs the first drive signals VTA1 to VTAn, which have a predetermined time difference (phase difference) from each other, to the first end-side terminals XA1 to XAn. The predetermined time difference (delay time) is variably set by, for example, a control signal coming from the transmission and receipt control unit 334 (FIG. 14) described below. So doing allows the first transmission circuit 510 to output the drive signals for carrying out the phase scanning.

The signal generation circuit 521, the voltage selection circuit 522, and the delay circuit 523 of the second transmission circuit 520 are similar to the signal generation circuit 511, the voltage selection circuit 512, and the delay circuit 513 of the first transmission circuit 510, and thus a more detailed description has been omitted. The two signal generation circuits 511 and 521 may however be consolidated into a single signal generation circuit. Either of the two voltage selection circuits 512, 522 may be omitted.

In this manner, according to the example of the first configuration for the first and second transmission circuits 510 and 520, the amplitude of the first drive signals VTA1 to VTAn and/or of the second drive signals VTB1 to VTBn can be variably set.

Figure 10:
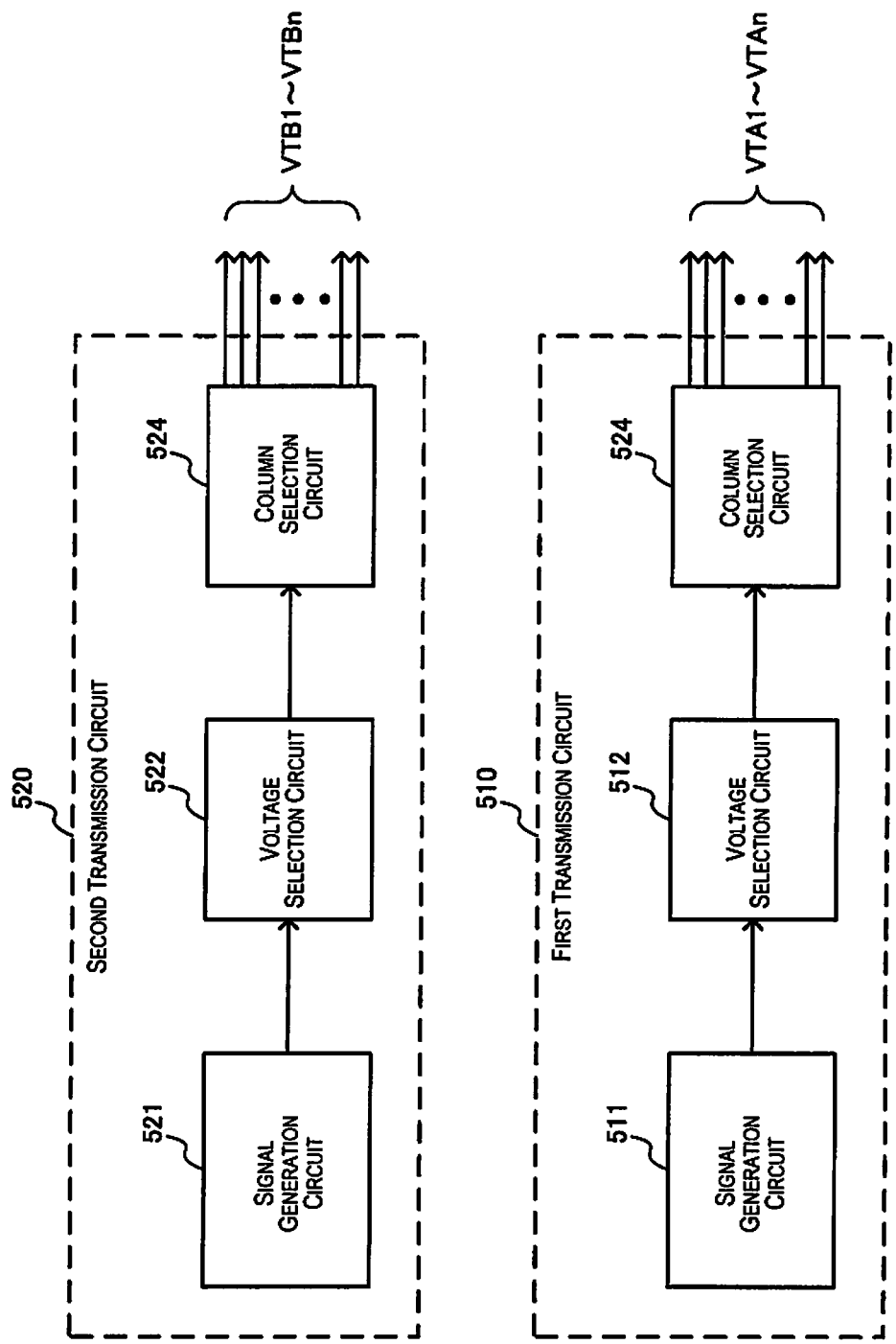
FIG. 10 is a second example of a configuration of a first and second transmission circuit.

FIG. 10 illustrates an example of a second configuration for the first and second transmission circuits 510, 520 of the present embodiment. The first transmission circuit 510 comprises the signal generation circuit 511, the voltage selection circuit 512, and a column selection circuit 514. The second transmission circuit 520 comprises the signal generation circuit 521, the voltage selection circuit 522, and a column selection circuit 524. The first and second transmission circuits 510 and 520 of the present embodiment are not limited to being the configuration of FIG. 10, but rather a variety of modifications can be implemented, such as omitting a part of the constituent elements thereof, replacing same with other constituent elements, or adding other constituent elements.

The signal generation circuit 511 and the voltage selection circuit 512 are the same as the example of the first configuration described above (FIG. 9), and thus a more detailed description thereof has been omitted.

The column selection circuit 514 receives the pulse signal coming from the voltage selection circuit 512, selects a plurality of terminals from among the first end-side terminals XA1 to XAn, and outputs the first drive signals to the selected terminals. For example, in a case where the first end-side terminals XA1 to XA4 are selected, the first drive signals VTA to VTA4 are outputted to the first end-side terminals XA1 to XA4. The selected terminals are variably set by, for example, a control signal coming from the transmission and receipt control unit 334 (FIG. 14) described below. So doing allows the first transmission circuit 510 to output the drive signals for carrying out the linear scanning.

The signal generation circuit 521, the voltage selection circuit 522, and the column selection circuit 524 of the second transmission circuit 520 are similar to the signal generation circuit 511, the voltage selection circuit 512, and the column selection circuit 514 of the first transmission circuit 510, and thus a more detailed description has been omitted. The two signal generation circuits 511 and 521 may however be consolidated into a single signal generation circuit. Either of the two voltage selection circuits 512, 522 may be omitted.

In this manner, according to the example of the second configuration for the first and second transmission circuits 510 and 520, the amplitude of the first drive signals VTA1 to VTAn and/or of the second drive signals VTB1 to VTBn can be variably set.

Figure 11:
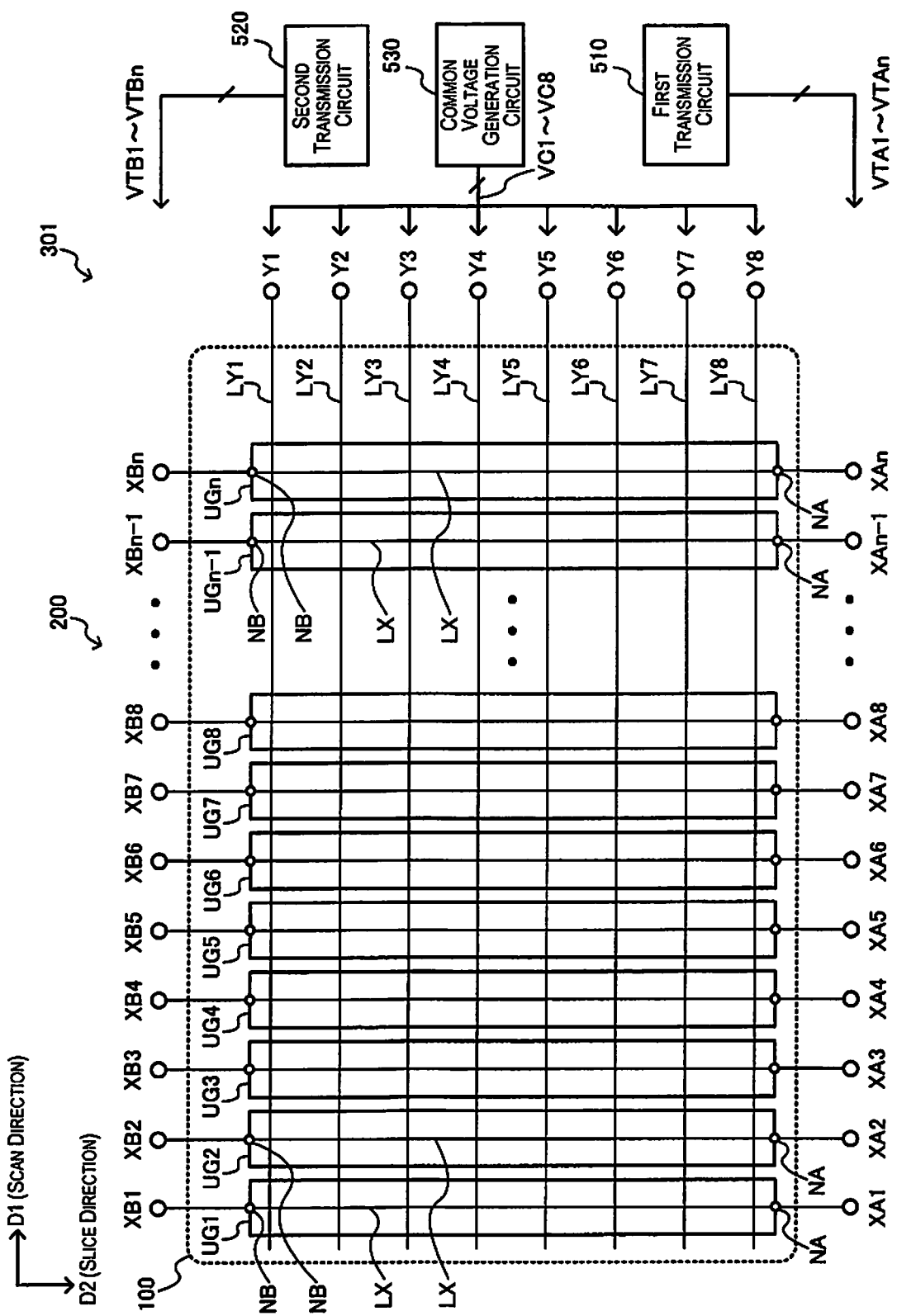
FIG. 11 is a second example of a configuration of an ultrasonic measurement apparatus.

FIG. 11 illustrates a second configuration example for the ultrasonic measurement apparatus 301 of the present embodiment. The second configuration example for the ultrasonic measurement apparatus 301 comprises the ultrasonic transducer device 200, the first transmission circuit 510, the second transmission circuit 520, and a common voltage generation circuit 530. The ultrasonic transducer device 200 comprises the ultrasonic element array 100, the first through n-th (where n is an integer two or greater) first end-side terminals XA1 to XAn, the first through n-th second end-side terminals XB1 to XBn, and first through m-th (where m is an integer two or greater) common voltage terminals Y1 to Ym. FIG. 11 illustrates a case where m=8, by way of example. The ultrasonic measurement apparatus 301 of the present embodiment is not limited to being the configuration of FIG. 11, but rather a variety of modifications can be implemented, such as omitting a part of the constituent elements thereof, replacing same with other constituent elements, or adding other constituent elements.

The ultrasonic element array 100, the first transmission circuit 510, and the second transmission circuit 520 are the same as in the first configuration example (FIG. 2) of the ultrasonic measurement apparatus 301 described above, and thus a more detailed description has been omitted.

The common voltage generation circuit 530 outputs a first through eighth (more broadly, first through m-th) mutually different common voltage VC1 to VC8 to the first through eighth (more broadly, first through m-th) common voltage terminals Y1 to Y8. The first through eighth common voltage terminals Y1 to Y8 are connected to one end of the first through eighth common electrode lines LY1 to LY8. So doing causes one of the first through eighth common voltages VC1 to VC8 to be supplied to the ultrasonic elements 10 belonging to each of the ultrasonic element groups of the ultrasonic element groups UG1 to UGn. The first through eighth common voltages VC1 to VC8 are, for example, VC1>VC2>VC3>. . . >VC8, or are VC1<VC2<VC3<. . . <VC8.

More specifically, in a case of, for example, the j-th ultrasonic element group UGj illustrated in FIG. 3A, then the first common voltage VC1 is supplied to the ultrasonic element 10-1, the second common voltage VC2 is supplied to the ultrasonic element 10-2, and the eighth common voltage VC8 is supplied to the ultrasonic element 10-8. For example, in a case where VC1>VC2>VC3>. . . >VC8, then the common voltage VC1 supplied to the ultrasonic element 10-1 is greatest, and the common voltage becomes gradually lower going toward the ultrasonic element 10-8. Conversely, in a case where VC1<VC2<VC3<. . . <VC8, then the common voltage VC1 supplied to the ultrasonic element 10-1 is lowest, and the common voltage becomes gradually higher going toward the ultrasonic element 10-8.

Figure 12:
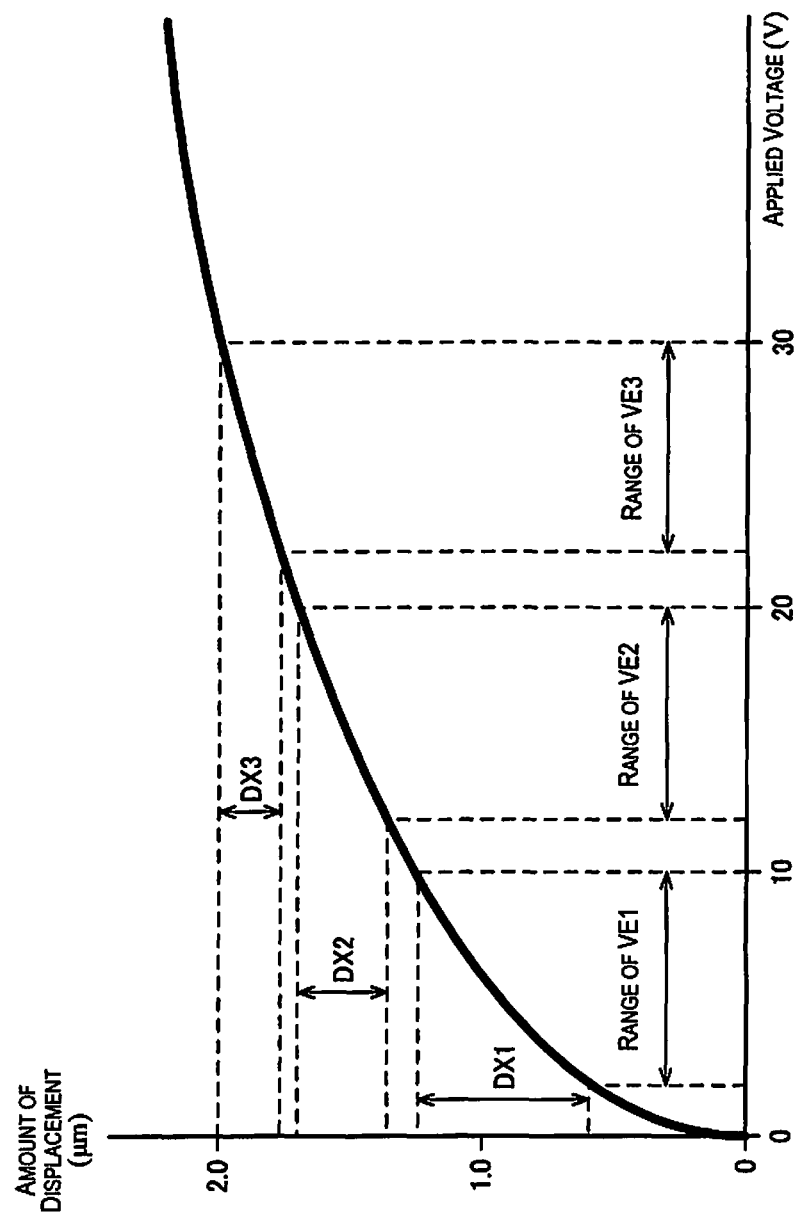
FIG. 12 is one example of the relationship between the voltage being applied to ultrasonic elements and the amount of displacement of the ultrasonic elements.

FIG. 12 illustrates one example of the relationship between the voltage (applied voltage) being applied to the ultrasonic elements and the amount of displacement of the ultrasonic elements. The horizontal axis is the applied voltage, and the vertical axis is the amount of displacement. As illustrated in FIG. 12, the relationship between the applied voltage and the amount of displacement is non-linear. In the following description, the first drive signal VTAj and the second drive signal VTBj being supplied to the j-th ultrasonic element group UGj are understood to be signals that have the same amplitude, and are denoted by a drive signal VDR for simplicity.

The voltage (applied voltage) applied to the piezoelectric body membrane 30 of the ultrasonic elements 10 is the difference VDR−VC between the drive signal voltage VDR and the common voltage VC, and thus when the VC is different, even with the same VDR, the applied voltage is different. The drive signal VDR is a signal for which the voltage changes at a predetermined frequency (a signal having an alternating current component), and in a case where, for example, the alternating component is a sine wave, then the VDR is given by the following formula as a function of time t.

$$VDR = VX \times \sin \omega t + VD \quad (2)$$

Herein, VX, ω, and VD are the voltage amplitude for the alternating current component, the angular frequency of the alternating current component, and the voltage of a direct current component.

The description now considers the three ultrasonic elements 10-1, 10-2, and 10-3, to each of which the VDR of formula is supplied and also to which the common voltages VC1, VC2, VC3, of mutually different voltages, are supplied. The applied voltages VE1, VE2, VE3 of the ultrasonic elements 10-1, 10-2, 10-3 are represented by the following formulae.

$$VE1 = VDR - VC1 = VX \times \sin \omega t + VD - VC1 \quad (3)$$

$$VE2 = VDR - VC2 = VX \times \sin \omega t + VD - VC2 \quad (4)$$

$$VE3 = VDR - VC3 = VX \times \sin \omega t + VD - VC3 \quad (5)$$

In a case where VC1>VC2>VC3, then the direct current component of each of the applied voltages will fall under the following relationship.

$$VD - VC1 < VD - VC2 < VD - VC3 \quad (6)$$

As such, the applied voltages VE1, VE2, VE3 vary within a range ±VX centered on the respective direct current components VD-VC1, VD-VC2, VD-VC3, as illustrated in FIG. 12. Because the relationship between the applied voltage and the amount of displacement is non-linear, DX1>DX2>DX3 holds true, where DX1, DX2, and DX3 are the amounts of displacement corresponding to VE1, VE2, and VE3, respectively. That is to say, the amount of displacement of the ultrasonic element 10-1 is greatest, and the amount of displacement decreases going from the ultrasonic element 10-1 toward the ultrasonic element 10-3. As such, the intensity of the ultrasonic waves emitted from the ultrasonic element 10-1 is greatest, and the intensity of the ultrasonic waves emitted decreases going from the ultrasonic element 10-1 toward the ultrasonic element 10-3. As a result thereof, the peak positions of the intensity distributions of the ultrasonic waves emitted can be shifted.

According to the second configuration example of the ultrasonic measurement apparatus 301, having the common voltages VC1 to VC6 supplied to the first through sixth common electrode lines LY1 to LY6 be VC1<VC2<. . . <VC6 makes it possible to set the peak positions of the intensity distributions of the ultrasonic waves to PK1, even in a case where the amplitude of the first drive signals VTA1 to VTA6 and the second drive signals VTB1 to VTB6 is the same, for example, in the phase scanning of FIGS. 5, 6, and 7. Having the common voltages VC1 to VC6 be VC1>VC2>. . . >VC6 also makes it possible to set the peak positions of the intensity distribution of the ultrasonic waves to PK2. Having the common voltages VC1 to VC6 be VC1=VC2=. . . =VC6 also makes it possible to set the peak positions of the intensity distribution of the ultrasonic waves to PK3. That is to say, setting the common voltages VC1 to VC6 to be set as described above makes it possible to set the scan plane to the first, second, or third set position SC1, SC2, or SC3.

Further, having the common voltages VC1 to VC6 be set as described above makes it possible to set the scan plane to the first, second, or third set position SC1, SC2, or SC3, even in a case where the amplitude of the first drive signals VTA1 to VTA6 and of the second drive signals VTB1 to VTB6 is the same, even in the linear scanning of FIG. 8.

In this manner, according to the second configuration example (FIG. 11) of the present embodiment, changing the difference between the amplitude of the first drive signals VTA1 to VTAn and the amplitude of the second drive signals VTB1 to VTBn using the first and second transmission circuits 510, 520 makes it possible to change the set position of the scan plane. The supplying of the common voltages VC1 to VCm of mutually different voltages by the common voltage generation circuit 530 also makes it possible to change the set position of the scan plane. As a result, it becomes possible to variably set the set position of the scan plane within a broader range.

Figure 13:
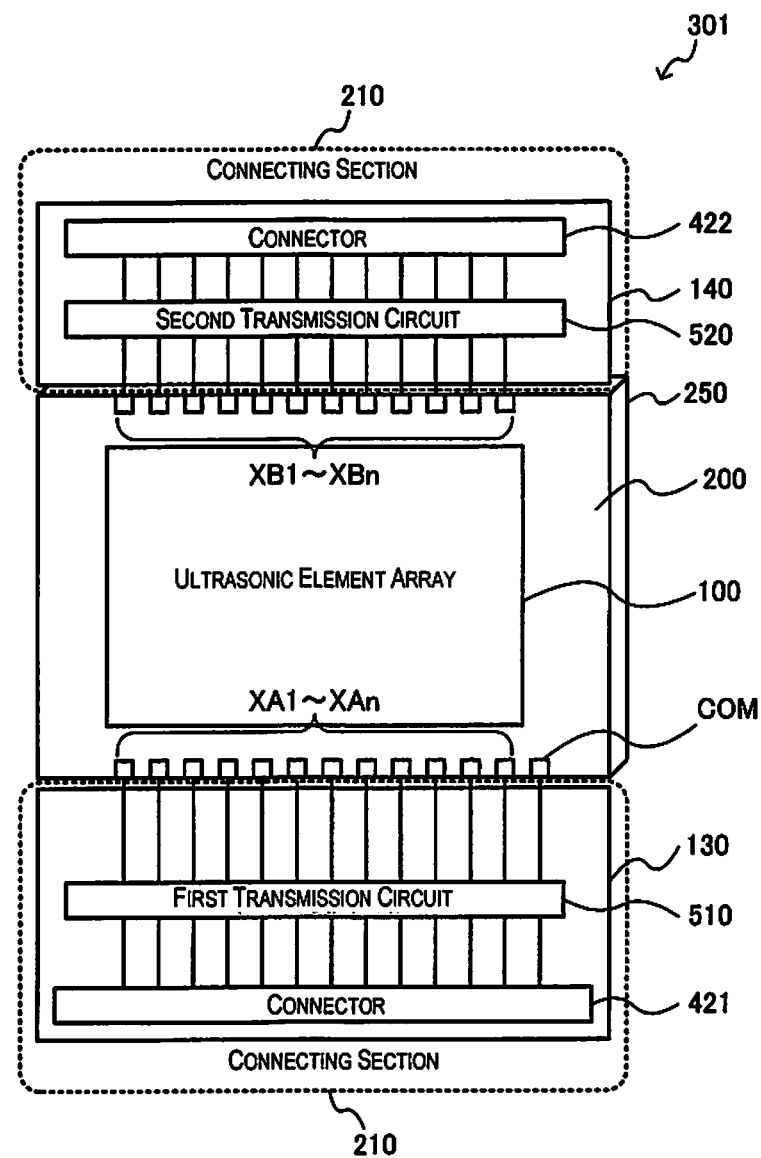
FIG. 13 is an example of an implementation of an ultrasonic measurement apparatus.

FIG. 13 illustrates an example of an implementation of the ultrasonic measurement apparatus 301 of the present embodiment. The example of implementation illustrated in FIG. 13 corresponds to the first configuration example of the ultrasonic measurement apparatus 301 illustrated in FIG. 2. The ultrasonic measurement apparatus 301 illustrated in FIG. 13 comprises the ultrasonic transducer device 200, a connecting section 210, and a support member 250. The ultrasonic measurement apparatus 301 of the present embodiment is not limited to being the configuration of FIG. 13, but rather a variety of modifications can be implemented, such as omitting a part of the constituent elements thereof, replacing same with other constituent elements, or adding other constituent elements.

The ultrasonic transducer device 200 comprises the ultrasonic element array 100, the first end-side terminals XA1 to XAn, the second end-side terminals XB1 to XBn, and the common voltage terminal COM. The ultrasonic transducer device 200 has already been described in FIG. 2, and thus a more detailed description is herein omitted.

The connecting section 210 is for electrically connecting a probe main body and the ultrasonic measurement apparatus 301, and includes connectors having a plurality of connection terminals, and flexible substrates on which is formed a wiring that connects the connector and the ultrasonic transducer device 200. More specifically, the connecting section 210 comprises a first connector 421 and a second connector 422 which serve as the connectors, and a first flexible substrate 130 and a second flexible substrate 140 serving as the flexible substrates.

The first transmission circuit 510 is implemented on the first flexible substrate 130. The first flexible substrate 130 is electrically connected to the first through n-th first end-side terminals XA1 to XAn, thereby electrically connecting the first transmission circuit 510 and the ultrasonic transducer device 200 together. The first transmission circuit 510 is also electrically connected to a processing apparatus 330 (FIG. 14), to be described below, via the first connector 421.

The second transmission circuit is implemented on the second flexible substrate 140. The second flexible substrate 140 is electrically connected to the first through n-th second end-side terminals XB1 to XBn, thereby electrically connecting the second transmission circuit 520 and the ultrasonic transducer device 200 together. The second transmission circuit 520 is also electrically connected to the processing apparatus 330 (FIG. 14), to be described below, via the second connector 422.

The support member 250 is a member for supporting the ultrasonic transducer device 200; the first and second connectors 421, 422 are provided to a first surface side of the support member 250, and the ultrasonic transducer device 200 is supported on a second surface side, which is the reverse side of the first surface side, of the support member 250.

The ultrasonic measurement apparatus 301 illustrated in FIG. 13 can be housed in a probe head 310 (FIG. 15C) to be described below. In such a case, the first and second flexible substrates 130, 140 could be bent toward the opposite direction of the direction of ultrasonic wave emission to house the ultrasonic measurement apparatus.

Providing the connecting section makes it possible to electrically connect the probe main body and the ultrasonic measurement apparatus 301, and makes it also possible for the ultrasonic measurement apparatus 301 to be attachable and detachable to/from the probe main body. Mounting the first and second transmission circuits 510, 520 onto the first and second flexible substrates 130, 140 also makes it possible to reduce the size of the ultrasonic measurement apparatus 301.

As has been described above, according to the ultrasonic measurement apparatus 301 of the present embodiment, it is possible to change the set position of the scan plane, which is the plane running along the scan direction of the beam of ultrasonic waves being emitted from the ultrasonic transducer device 200. So doing makes it possible to set a plurality of scan planes along, for example, the slice direction, and to obtain a plurality of cross-sectional images by scanning the ultrasonic wave beams along each of the scan planes. As a result, it becomes possible to implement the ultrasonic measurement apparatus 301 enabling efficient scanning with a simple configuration.

Figure 14:
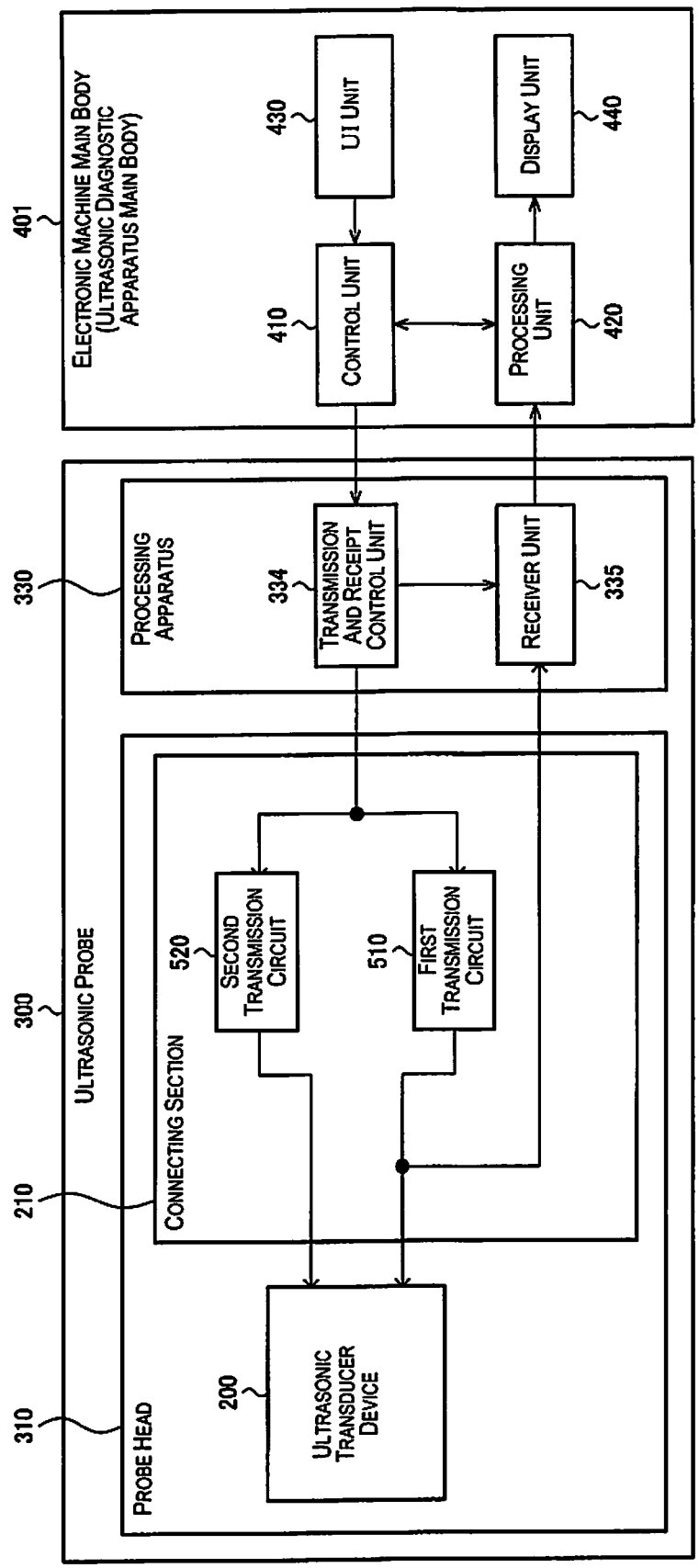
FIG. 14 is an example of a basic configuration for an electronic machine (an ultrasonic diagnostic apparatus)

3. Probe Head, Ultrasonic Probe, Electronic Machine, and Ultrasonic Diagnostic apparatus FIG. 14 illustrates an example of a basic configuration for an electronic machine (ultrasonic diagnostic apparatus) 400 of the present embodiment.

The ultrasonic diagnostic apparatus 400 comprises an ultrasonic probe 300 and an ultrasonic diagnostic apparatus main body 401. The ultrasonic probe 300 comprises the probe head 310 and the processing apparatus 330. The ultrasonic diagnostic apparatus main body 401 comprises a control unit 410, a processing unit 420, a user interface unit (UI unit) 430, and a display unit 440.

The probe head 310 comprises the ultrasonic measurement apparatus 301. The ultrasonic measurement apparatus 301 comprises the ultrasonic transducer device 200 as well as the connection section 210 (connector section) for connecting the ultrasonic transducer device 200 to a circuit board (for example, a rigid substrate). Implemented on the circuit board are the transmission and receipt control unit 334 and a receiver unit 335. Implemented on the connecting section 210 are the first and second transmission circuits 510, 520.

The processing apparatus 330 comprises the transmission and receipt control unit 334 and the receiver unit 335 (an analog front end unit). In a case where ultrasonic waves are to be transmitted, the transmission and receipt control unit 334 issues a transmission command to the first and second transmission circuits 510, 520, and the first and second transmission circuits receive the transmission command and output the first and second drive signals. The receiver unit 335 includes a limiter circuit (not shown), and the limiter circuit cuts off the drive voltage. In a case where reflected waves of the ultrasonic waves are received, the receiver unit 335 receives a signal of the reflected waves detected by the ultrasonic transducer device 200. The receiver unit 335 processes (for example, amplification processing, A/D conversion processing, or the like) the signal of the reflected waves on the basis of a receipt command coming from the transmission and receipt control unit 334, and transmits the processed signal to the processing unit 420. The processing unit 420 generates display image data on the basis of the signal, and causes the display unit 440 to produce a display.

The ultrasonic measurement apparatus 301 of the present embodiment is not limited to being a medical ultrasonic diagnostic apparatus such as described above, but rather can be applied to a variety of electronic machines. Conceivable examples of electronic machines to which the ultrasonic measurement apparatus 301 of the present embodiment has been applied would include a diagnostic machine for non-destructively inspecting the interior of a building or the like, or a user interface machine for detecting the movement of a user's finger by the reflection of ultrasonic waves.

Figure 15A:
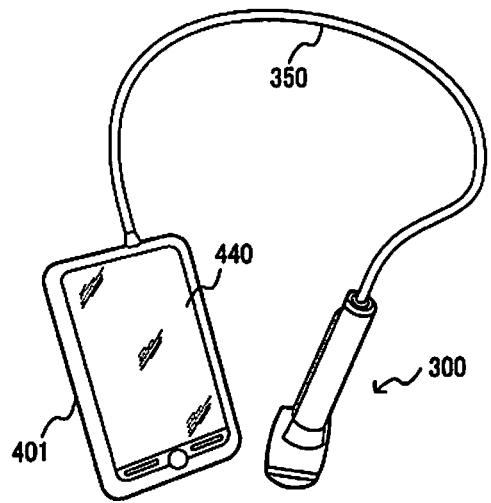
FIG. 15A is an example of a specific configuration for an ultrasonic diagnostic apparatus.
Figure 15B:
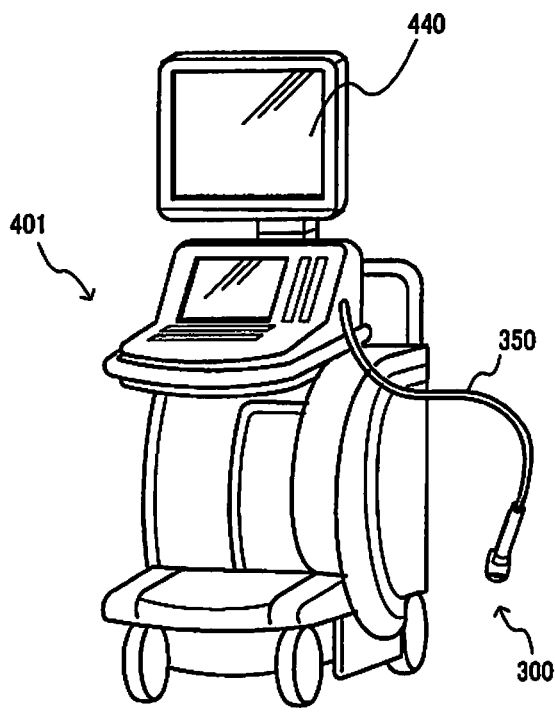
FIG. 15B is the example of the specific configuration for the ultrasonic diagnostic apparatus.

FIGS. 15A and 15B illustrate a specific configuration example for the ultrasonic diagnostic apparatus 400 of the present embodiment. FIG. 15A illustrates a portable ultrasonic diagnostic apparatus 400, and FIG. 15B illustrates a floor-standing ultrasonic diagnostic apparatus 400.

Both the portable version and the floor-standing version of the ultrasonic diagnostic apparatus 400 include the ultrasonic probe 300, a cable 350, and the ultrasonic diagnostic apparatus main body 401. The ultrasonic probe 300 is connected to the ultrasonic diagnostic apparatus main body 401 by the cable 350. The ultrasonic diagnostic apparatus main body 401 includes the display unit 440 for displaying the display image data.

Figure 15C:
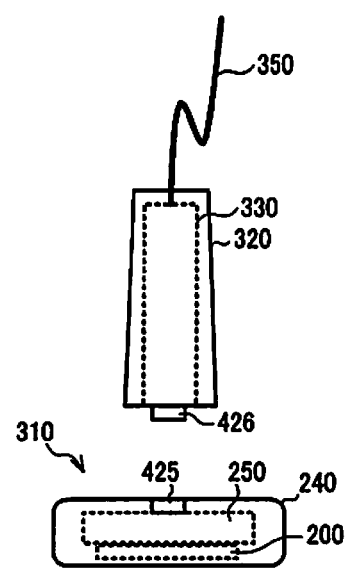
FIG. 15C is an example of a specific configuration for an ultrasonic probe.

FIG. 15C illustrates a specific configuration example for the ultrasonic probe 300 of the present embodiment. The ultrasonic probe 300 comprises the probe head 310 and the probe main body 320, and, as illustrated in FIG. 15C, the probe head 310 can be attached or detached to/from the probe main body 320.

The probe head 310 comprises the ultrasonic measurement apparatus 301, a probe housing 240, and a probe head-side connector 425. The ultrasonic measurement apparatus 301 comprises the ultrasonic transducer device 200, the connecting section 210, and the support member 250.

The probe main body 320 comprises the processing apparatus 330 and a probe main body-side connector 426. The probe main body-side connector 426 is connected to the probe head-side connector 425. The probe main body 320 is connected to the ultrasonic diagnostic apparatus main body 401 by the cable 350.

Though the present embodiment has been described in greater detail above, it shall be readily understood by a person skilled in the art that there are numerous possible modifications which do not substantially depart from the novel features and effects of the present invention. As such, the modification examples of such description are understood to all also be included in the scope of the present invention. For example, a phrase mentioned at least once in the specification or accompanying drawings together with a different phrase of broader or similar meaning can also be replaced with the different phrase in any portion in the specification or accompanying drawings. The configurations and operation of the probe head, the ultrasonic probe, the electronic machine, and the ultrasonic diagnostic apparatus are also not limited to those described in the present embodiment, but rather a variety of modifications can be implemented.

The entire disclosure of Japanese Patent Application No. 2012-229586, filed Oct. 17, 2012 is expressly incorporated by reference herein.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic measurement apparatus comprising:
    an ultrasonic transducer device including an ultrasonic element array, a first first end-side terminal through an n-th (where n is an integer two or greater) first end-side terminal provided to a first end side of the ultrasonic element array, and a first second end-side terminal through an n-th second end-side terminal provided to a second end side of the ultrasonic element array opposing the first end side of the ultrasonic element array;
    a first drive electrode line through an n-th drive electrode line, each drive electrode line having a first end and a second end, the first end being connected to the first end-side terminal and the second end being connected to the second end-side terminal;
    a first transmission circuit configured to output first drive signals to the first first end-side terminal through the n-th first end-side terminal; and
    a second transmission circuit configured to output second drive signals to the first second end-side terminal through the n-th second end-side terminal,
    an amplitude of at least one of the first drive signals and the second drive signals being variably set.

2. The ultrasonic measurement apparatus as set forth in claim 1, wherein
    a set position of a scan plane, which is a plane running along a direction of scanning of a beam of ultrasonic waves emitted from the ultrasonic transducer device, is changed by changing of a difference between an amplitude of the first drive signals and an amplitude of the second drive signals by at least one of the first transmission circuit and the second transmission circuit.

3. The ultrasonic measurement apparatus according to claim 2, wherein
    the at least one of the first transmission circuit and the second transmission circuit sets the scan plane to a first set position by causing the amplitude of the first drive signals to be greater than the amplitude of the second drive signals, and
    sets the scan plan to a second set position different from the first set position by causing the amplitude of the first drive signals to be less than the amplitude of the second drive signals.

4. The ultrasonic measurement apparatus according to claim 3, wherein
    the at least one of the first transmission circuit and the second transmission circuit sets the scan plane to a third set position between the first set position and the second set position, by causing the amplitude of the first drive signals and the amplitude of the second drive signals to be the same.

5. The ultrasonic measurement apparatus according to claim 1, wherein
    the first transmission circuit outputs the first drive signals, which are for carrying out a phase scanning, and
    the second transmission circuit outputs the second drive signals, which are for carrying out the phase scanning.

6. The ultrasonic measurement apparatus according to claim 1, wherein
    the first transmission circuit outputs the first drive signals, which are for carrying out a linear scanning, and
    the second transmission circuit outputs the second drive signals, which are for carrying out the linear scanning.

7. The ultrasonic measurement apparatus according to claim 1, further comprising
    a first flexible substrate connected to the first first end-side terminal through the n-th first end-side terminal, and
    a second flexible substrate connected to the first second end-side terminal through the n-th second end-side terminal, wherein
    the first transmission circuit is implemented on the first flexible substrate, and the second transmission circuit is implemented on the second flexible substrate.

8. The ultrasonic measurement apparatus according to claim 1, wherein
    the ultrasonic element array includes a first ultrasonic element group through an n-th ultrasonic element group arranged along a first direction,
    a first end-side node of a j-th (where j is an integer $1 \leq j \leq n$) ultrasonic element group of the first ultrasonic element group through the n-th ultrasonic element group is connected to a j-th first end-side terminal of the first first end-side terminal through the n-th first end-side terminal,
    a second end-side node of the j-th ultrasonic element group is connected to a j-th second end-side terminal of the first second end-side terminal through the n-th second end-side terminal,
    the j-th ultrasonic element group includes
        a plurality of ultrasonic elements, and
        a drive electrode line which is arranged along a second direction intersecting the first direction, a first end of which is connected to the first end-side node, and a second end of which is connected to the second end-side node, and
    a first electrode belonging to each of the plurality of the ultrasonic elements of the j-th ultrasonic element group is connected to the drive electrode line.

9. The ultrasonic measurement apparatus according to claim 8, further comprising a common voltage generation circuit configured to output common voltages, wherein the ultrasonic transducer device includes a first common voltage terminal through an m-th (where m is an integer two or greater) common voltage terminal, the ultrasonic element array includes a first common electrode line through an m-th common electrode line arranged along the first direction and connected to the first common voltage terminal through the m-th common voltage terminal, a second electrode belonging to each of the plurality of the ultrasonic elements of the j-th ultrasonic element group is connected to one of the first common electrode line through the m-th common electrode line, and the common voltage generation circuit outputs the common voltages to the first common voltage terminal through the m-th common voltage terminal, with the common voltages output to the first common voltage terminal through the m-th common voltage terminal being different from each other.

10. The ultrasonic measurement apparatus according to claim 8, wherein the ultrasonic transducer device includes a substrate on which a plurality of openings are arranged in an arrayed shape, each of the plurality of the ultrasonic elements belonging to the j-th ultrasonic element group is provided to each of the plurality of the openings, each of the plurality of the ultrasonic elements includes
a vibrating membrane blocking one of the openings, and
a piezoelectric element section provided on the vibrating membrane, the piezoelectric element section includes
a lower electrode provided on the vibrating membrane,
a piezoelectric body membrane at least partially covering the lower electrode, and
an upper electrode at least partially covering the piezoelectric body membrane, and the first electrode is either the upper electrode or the lower electrode.

11. A probe head comprising the ultrasonic measurement apparatus according to claim 1.

12. An ultrasonic probe comprising:
the probe head according to claim 11, and
a processing apparatus configured to process a signal coming from the ultrasonic measurement apparatus.

13. An electronic machine comprising the ultrasonic probe according to claim 12.

14. An ultrasonic diagnostic apparatus comprising:
the ultrasonic probe according to claim 13, and
a display unit configured to display image data.

15. An ultrasonic measurement apparatus comprising:
an ultrasonic transducer device including an ultrasonic element array, a first first end-side terminal through an n-th (where n is an integer two or greater) first end-side terminal provided to a first end side of the ultrasonic element array, and a first second end-side terminal through an n-th second end-side terminal provided to a second end side of the ultrasonic element array opposing the first end side of the ultrasonic element array;
a first drive electrode line through an n-th drive electrode line, each drive electrode line having a first end and a second end, the first end being connected to the first end-side terminal and the second end being connected to the second end-side terminal; and
a common voltage generation circuit configured to output common voltages,
wherein
the ultrasonic transducer device includes a first common voltage terminal through an m-th (where m is an integer two or greater) common voltage terminal, the ultrasonic element array includes a first common electrode line through an m-th common electrode line arranged along a first direction and connected to the first common voltage terminal through the m-th common voltage terminal, a second electrode belonging to each of the plurality of the ultrasonic elements of a j-th ultrasonic element group (where j is an integer $1 \leq j \leq n$) is connected to one of the first common electrode line through the m-th common electrode line, and the common voltage generation circuit outputs the common voltages to the first common voltage terminal through the m-th common voltage terminal, with the common voltages output to the first common voltage terminal through the m-th common voltage terminal being different from each other.

16. The ultrasonic measurement apparatus as set forth in claim 1, wherein the first transmission circuit and the second transmission circuit are configured to output the first drive signals and the second drive signals, respectively, to one of the first drive electrode line through the n-th drive electrode line at the same timing.

17. The ultrasonic measurement apparatus as set forth in claim 1, wherein
each of the first transmission circuit and the second transmission circuit includes a pulse generator.

* * * * *